(12) United States Patent
Kruse

(10) Patent No.: US 12,372,648 B2
(45) Date of Patent: Jul. 29, 2025

(54) SPARSE SYNTHETIC APERTURE ULTRASOUND METHODS AND SYSTEMS

(71) Applicant: Decision Sciences Medical Company, LLC, Poway, CA (US)

(72) Inventor: Dustin E. Kruse, Grand Island, NY (US)

(73) Assignee: DECISION SCIENCES MEDICAL COMPANY, LLC, Poway, CA (US)

(*) Notice: Subject to any disclaimer, the term of this patent is extended or adjusted under 35 U.S.C. 154(b) by 264 days.

(21) Appl. No.: 17/881,474

(22) Filed: Aug. 4, 2022

(65) Prior Publication Data
US 2023/0052016 A1  Feb. 16, 2023

Related U.S. Application Data

(60) Provisional application No. 63/230,941, filed on Aug. 9, 2021.

(51) Int. Cl.
  *G01S 15/89* (2006.01)
  *A61B 8/00* (2006.01)
  (Continued)

(52) U.S. Cl.
  CPC ........ *G01S 15/8997* (2013.01); *A61B 8/4488* (2013.01); *A61B 8/483* (2013.01);
  (Continued)

(58) Field of Classification Search
  CPC ............ G01S 15/8997; G01S 7/52047; G01S 15/8915; G01S 15/8925; G01S 15/8927;
  (Continued)

(56) References Cited

U.S. PATENT DOCUMENTS

| 4,159,462 A | 6/1979 | Rocha et al. |
| 5,107,837 A | 4/1992 | Ophir et al. |

(Continued)

FOREIGN PATENT DOCUMENTS

| AU | 2016233279 A1 * | 11/2017 | ........... A61B 8/4461 |
| CA | 3080561 A1 * | 5/2019 | ........... A61B 8/4488 |

(Continued)

OTHER PUBLICATIONS

Lockwood et al., Real-Time 3-D Ultrasound Imaging Using Sparse Synthetic Aperture Beamforming, IEEE transactions on ultrasonics, ferroelectrics, and frequency control, vol. 45, No. 4, Jul. 1998 (Year: 1998).*

(Continued)

*Primary Examiner* — Daniel Pihulic
(74) *Attorney, Agent, or Firm* — Perkins Coie LLP

(57) ABSTRACT

Systems, devices, and methods for sparse synthetic aperture ultrasound (SSAU) imaging and/or range-Doppler applications are described. An example method for SAU imaging includes receiving, via a user interface, an input including an array topology comprising a particular N-dimensional arrangement of a plurality of transducer elements of the SAU system, an objective space, a function characterizing an imaging capability of the SAU system, and one or more constraints, generating, based on the input, an acoustic field over the objective space for each of the plurality of transducer elements of the array topology, selecting one or more transducer elements from the plurality of transducer elements of the array topology based on evaluation of the function, and providing for display, on the user interface, the selected one or more transducer elements that satisfy each of the one or more constraints.

19 Claims, 18 Drawing Sheets

(51) Int. Cl.
*B06B 1/02* (2006.01)
*G01S 7/52* (2006.01)
(52) U.S. Cl.
CPC ...... *G01S 7/52047* (2013.01); *G01S 15/8915* (2013.01); *G01S 15/8925* (2013.01); *G01S 15/8927* (2013.01); *B06B 1/0292* (2013.01)
(58) Field of Classification Search
CPC ..... A61B 8/4488; A61B 8/483; A61B 8/5207; A61B 8/54; B06B 1/0292
See application file for complete search history.

(56) References Cited

U.S. PATENT DOCUMENTS

| | | | |
|---|---|---|---|
| 6,736,780 B2 | 5/2004 | Song et al. | |
| 7,066,886 B2 | 6/2006 | Song et al. | |
| 7,319,641 B2 * | 1/2008 | Goudie | H04R 1/403 367/138 |
| 7,963,919 B2 * | 6/2011 | Proulx | G01S 15/8925 600/443 |
| 8,939,909 B2 | 1/2015 | Wegner | |
| 9,503,201 B2 * | 11/2016 | Saulnier | H04R 31/00 |
| 9,844,359 B2 * | 12/2017 | Wegner | A61B 8/14 |
| 10,321,889 B2 | 6/2019 | Wegner | |
| 11,096,661 B2 | 8/2021 | Wegner | |
| 11,154,274 B2 * | 10/2021 | Wegner | A61K 49/226 |
| 11,520,043 B2 * | 12/2022 | Kruse | G10K 11/346 |
| 11,607,192 B2 | 3/2023 | Wegner | |
| 11,860,273 B2 * | 1/2024 | Kruse | A61B 8/587 |
| 12,121,394 B2 | 10/2024 | Wegner | |
| 2003/0125628 A1 | 7/2003 | Song et al. | |
| 2005/0004465 A1 | 1/2005 | Abuhamad | |
| 2005/0101867 A1 | 5/2005 | Johnson et al. | |
| 2007/0156050 A1 | 7/2007 | Barnes et al. | |
| 2007/0167752 A1 * | 7/2007 | Proulx | G01S 15/8925 600/437 |
| 2007/0239002 A1 | 10/2007 | Alam | |
| 2008/0110263 A1 | 5/2008 | Klessel et al. | |
| 2009/0030312 A1 * | 1/2009 | Hadjicostis | A61B 8/4488 606/33 |
| 2012/0281507 A1 | 11/2012 | Rikoski | |
| 2016/0270763 A1 * | 9/2016 | Hayes | A61B 8/54 |
| 2020/0284902 A1 * | 9/2020 | Kruse | G10K 11/346 |
| 2020/0337674 A1 * | 10/2020 | Wegner | A61K 49/226 |
| 2021/0361259 A1 * | 11/2021 | Wegner | A61B 8/4422 |
| 2022/0155440 A1 * | 5/2022 | Kruse | G10K 11/348 |
| 2023/0052016 A1 * | 2/2023 | Kruse | A61B 8/54 |
| 2023/0089137 A1 * | 3/2023 | Kruse | A61B 8/54 600/447 |

FOREIGN PATENT DOCUMENTS

| | | | | |
|---|---|---|---|---|
| CA | 3001315 C | * | 12/2023 | ............ A61B 34/20 |
| CN | 107530061 A | * | 1/2018 | ........... A61B 8/4461 |
| CN | 108366775 A | * | 8/2018 | ............ A61B 34/20 |
| CN | 116685847 A | * | 9/2023 | ............. A61B 8/145 |
| EP | 1795917 A2 | * | 6/2007 | ............. A61B 8/483 |
| JP | 55051351 A | | 4/1980 | |
| JP | 58195550 A | | 11/1983 | |
| JP | 60048736 A | | 3/1985 | |
| JP | 2004147852 A | | 5/2004 | |
| JP | 2013520235 | | 6/2013 | |
| WO | 2013066821 | | 5/2013 | |
| WO | WO-2016149427 A1 | * | 9/2016 | ........... A61B 8/4461 |
| WO | WO-2018061025 A1 | * | 4/2018 | ......... G01S 15/8915 |
| WO | WO-2019084526 A1 | * | 5/2019 | ........... A61B 8/4488 |
| WO | WO-2020219705 A1 | * | 10/2020 | ........... A61B 8/4281 |
| WO | WO-2022104230 A1 | * | 5/2022 | ............. A61B 8/145 |

OTHER PUBLICATIONS

European Search Report mailed on Apr. 19, 2017 for European Application No. 14844538.0, filed on Sep. 9, 2014 (10 pages).
Examination Report mailed on Dec. 20, 2019 for Europe Patent Application No. 14844538.0, filed on Sep. 9, 2014 (7 pages).
First Examination Report mailed Dec. 7, 2018 for Australian Patent Application No. 2018203912, filed on Sep. 9, 2014, 2 pages.
International Search Report and Written Opinion mailed on Mar. 3, 2015 for International Application No. PCT/US2014/054855, filed on Sep. 9, 2014 (11 pages).
Office Action mailed Mar. 17, 2020 for Japanese Application No. 2018-145683, filed on Sep. 9, 2014 (4 pages).
Office Action mailed Mar. 25, 2020 for Japanese Application No. 2016-542050, filed on Sep. 9, 2014 (4 pages).
Office Action mailed Oct. 29, 2019 for Japanese Application No. 2018-145683, filed on Sep. 9, 2014 (3 pages).
Office Action mailed on Jun. 11, 2019 for Japanese Application No. 2016-542050, filed on Sep. 9, 2014 (15 pages).
Office Action mailed on Jun. 18, 2019 for Japanese Patent Application No. 2018-145683, filed on Sep. 9, 2014, 12 pages.
Office Action mailed on Jun. 5, 2018 for Chinese Patent Application No. 201480062224.3, filed on Sep. 9, 2014, 13 pages.
Office Action mailed on Sep. 19, 2017 for Japanese Application No. 2016-542050, filed on Sep. 9, 2014 (15 pages).
Singapore Written Opinion mailed on Jul. 10, 2017 for Singapore Application No. 11201601906P, filed on Sep. 9, 2014 (8 pages).

* cited by examiner

SPARSE SYNTHETIC APERTURE ULTRASOUND METHODS AND SYSTEMS

CROSS-REFERENCE TO RELATED SYSTEMS

This patent document claims priorities to and benefits of U.S. Provisional Patent Application No. 63/230,941 titled "SPARSE SYNTHETIC APERTURE ULTRASOUND METHODS AND SYSTEMS" and filed on Aug. 9, 2021. The entire content of the before-mentioned patent application is incorporated by reference as part of the disclosure of this document for all purposes.

TECHNICAL FIELD

This patent document relates to systems, devices, and processes that use acoustic energy for imaging technologies applicable to various medical imaging modalities.

BACKGROUND

Acoustic imaging is an imaging modality that employs the properties of sound waves traveling through a medium to render a visual image of structures that scatter sound waves within the medium. High frequency acoustic imaging has been used as an imaging modality for decades in a variety of biomedical fields to view internal structures and functions of animals and humans. High frequency acoustic waves used in biomedical imaging may operate in different frequencies, e.g., between 1 and 20 MHz, or even higher frequencies, and are often termed ultrasound waves. Compared to other imaging modalities, the real-time, non-ionizing, portable, and relatively low-cost features of ultrasound imaging make it attractive for biomedical applications.

SUMMARY

Disclosed are systems, devices, and methods for sparse synthetic aperture ultrasound (SSAU) imaging applications. In some embodiments, the SSAU disclosed systems and methods generate an optimized pair of mutually exclusive apertures that operate with multiple aperture openings such that the resulting point spread function is optimized for each combination of aperture openings and operable for focusing over multiple ranges and steering angles. In some implementations, the disclosed SSAU systems and methods can be used in acoustic imaging applications.

In an example embodiment, a method for SAU imaging includes receiving, via a user interface, an input including an array topology comprising a particular N-dimensional arrangement of a plurality of transducer elements of the SAU system, an objective space comprising a sampled three-dimensional space adjacent to and non-overlapping with a space occupied the array topology, a function characterizing an imaging capability of the SAU system, and one or more constraints on at least one physical characteristic of the plurality of transducer elements, wherein N is a positive integer, generating, based on the input, an acoustic field over the objective space for each of the plurality of transducer elements of the array topology, selecting one or more transducer elements from the plurality of transducer elements of the array topology that corresponds to the function that is being evaluated (e.g., being optimized) subject to the one or more constraints, the one or more transducer elements corresponding to a plurality of transmit apertures and a plurality of receive apertures, and providing for display, on the user interface, the selected one or more transducer elements that satisfy each of the one or more constraints.

In another example embodiment, an apparatus comprising a memory and a processor implements the above-described method is disclosed.

In yet another example embodiment, the method may be embodied as processor-executable code and may be stored on a non-transitory computer-readable program medium.

The subject matter described in this patent document can be implemented in ways that produce an optimized sparse array for synthetic aperture operation that may be steered and focused within the near-field of the aperture without deleterious image artifacts caused by sidelobes and grating lobes.

DETAILED DESCRIPTION

Figure 1:
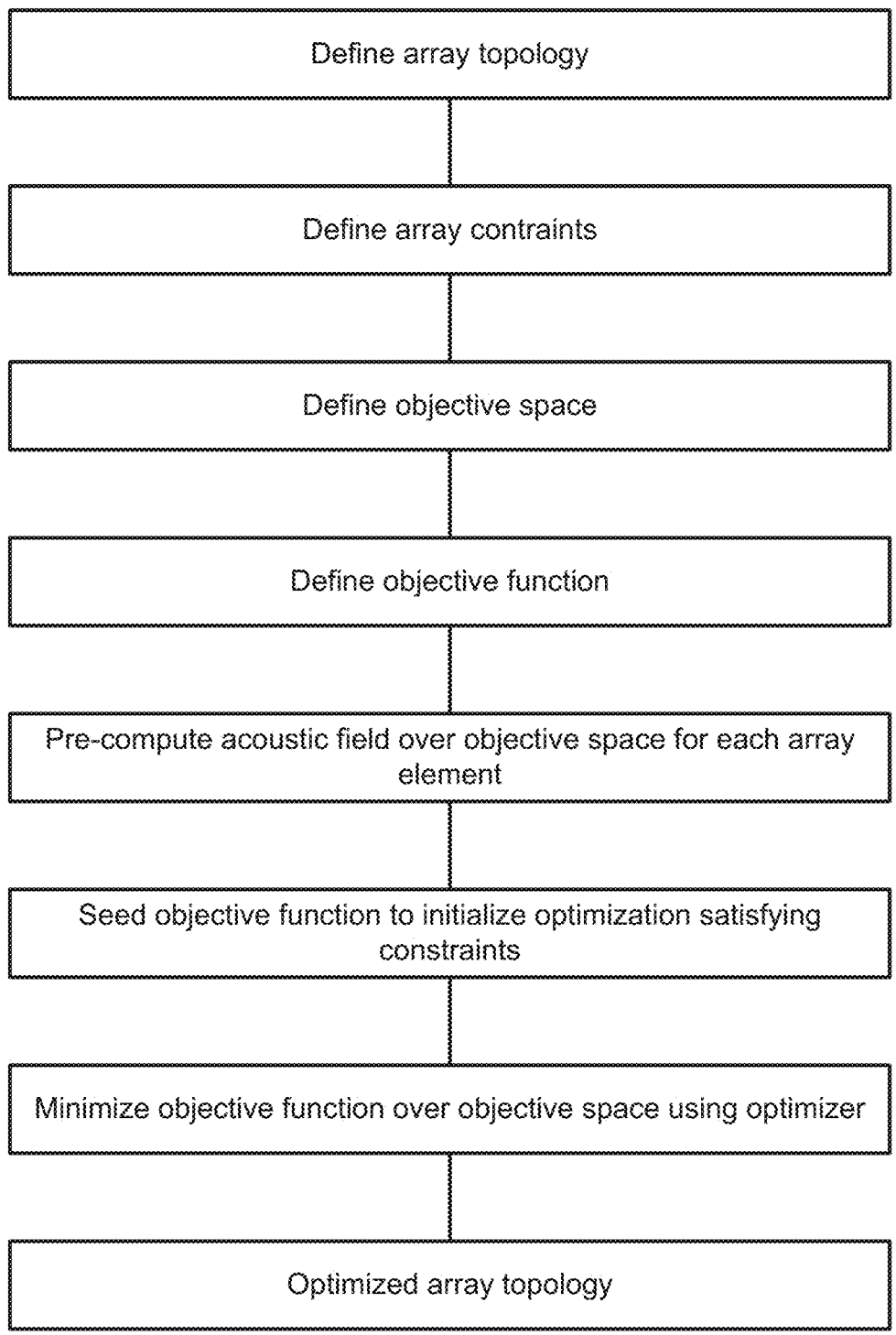
FIG. 1 is a flow diagram of an algorithm of a method for SSAU imaging optimization in accordance with the present technology.
Figure 2:
FIG. 2 illustrates examples 1D and 2D topologies for sparse aperture optimization.
Figure 2:
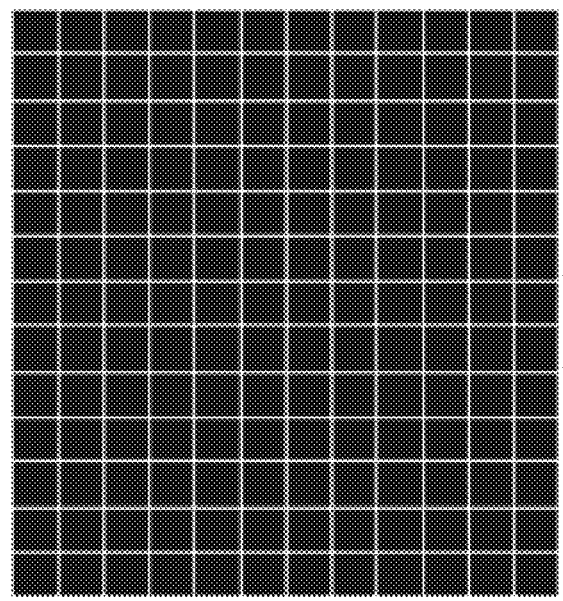
Figure 2:
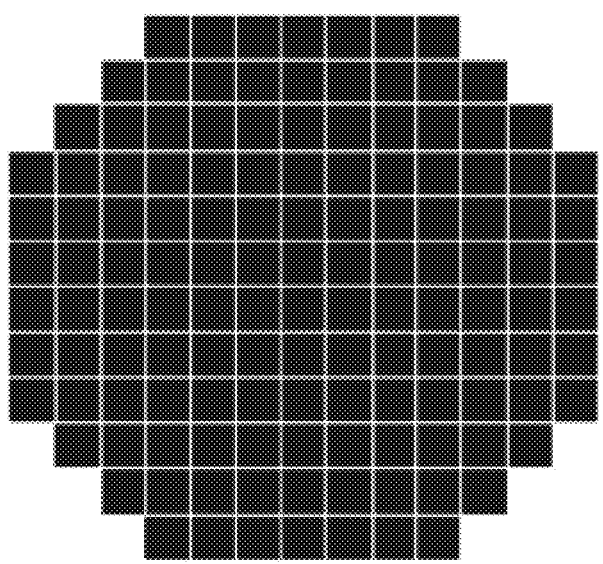
Figure 3:
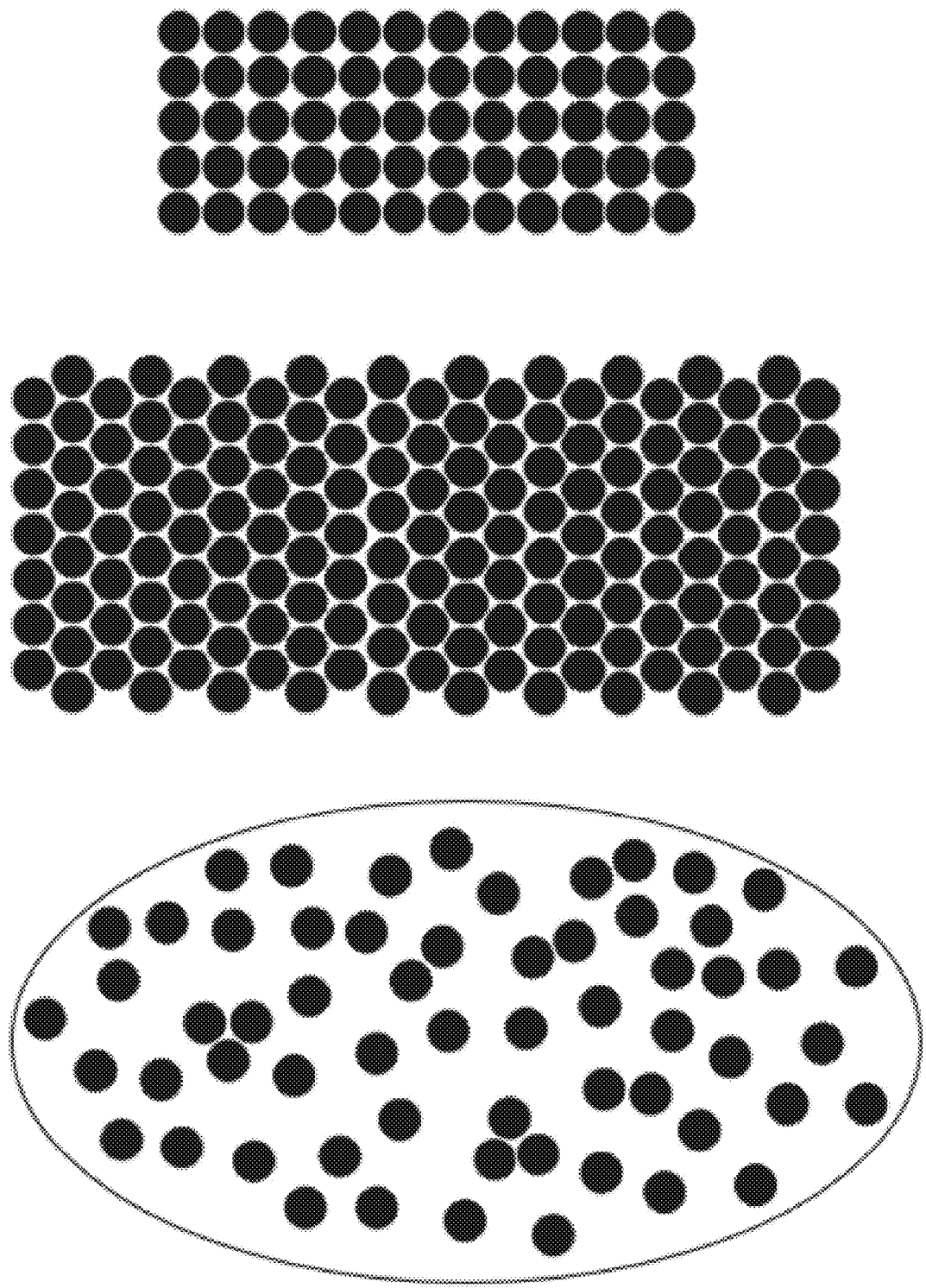
FIG. 3 illustrates other examples of 2D topologies for sparse aperture optimization.
Figure 4:
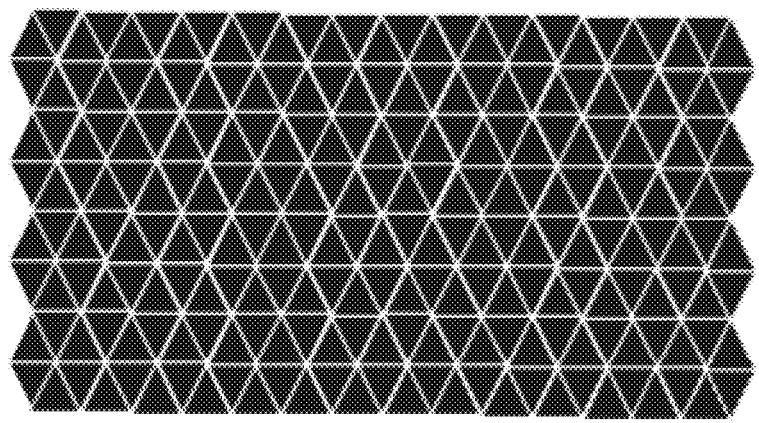
FIG. 4 illustrates other examples of 2D topologies for sparse aperture optimization.
Figure 4:
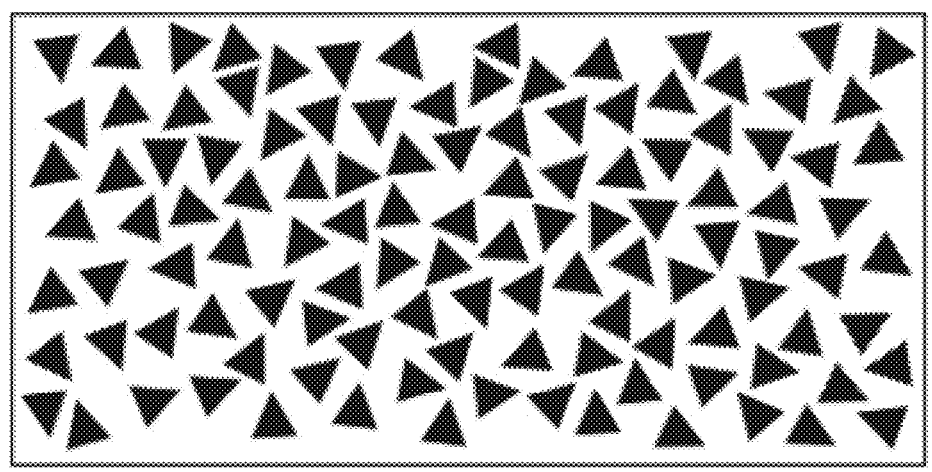
Figure 4:
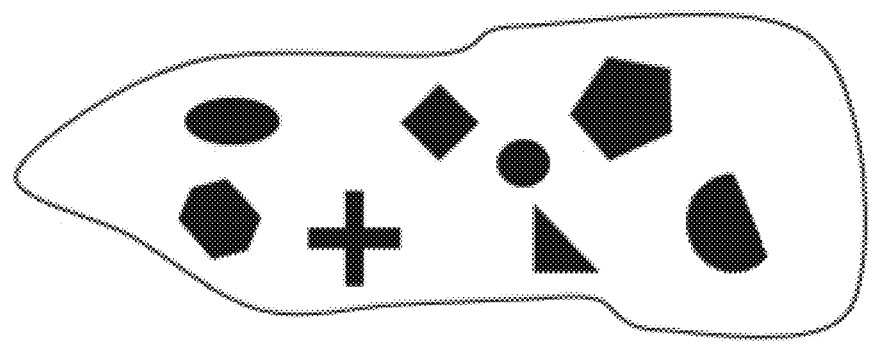
Figure 5:
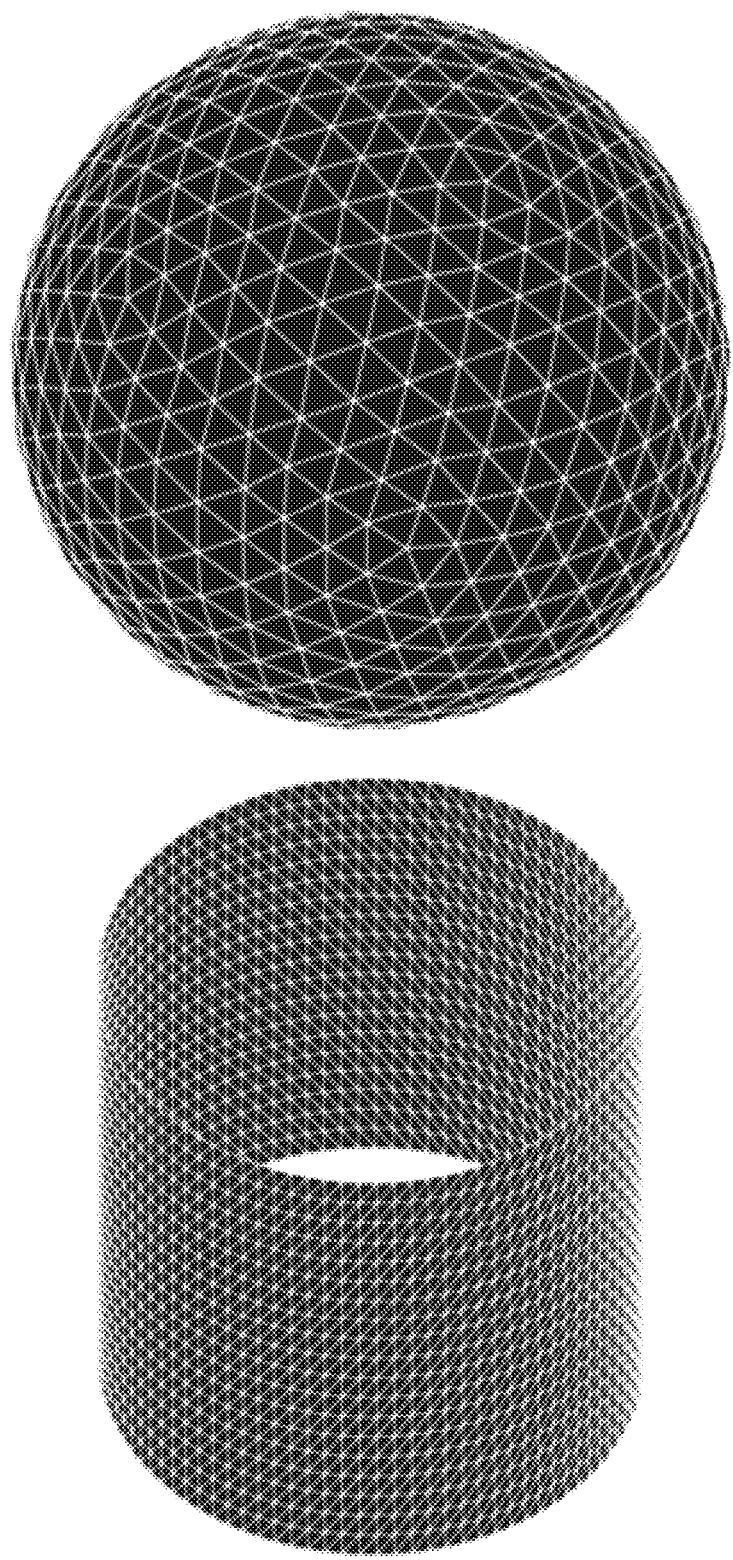
FIG. 5 illustrates examples of 3D topologies for sparse aperture optimization.

Ultrasound imaging operates the same principle as sound navigation and ranging (SONAR) in which a transmission of one or more acoustic waves results in one or more echoes from structures that are received and processed to form an image. Some factors, including inadequate spatial resolution and tissue differentiation, can lead to less than desirable image quality using conventional techniques of ultrasound imaging, which can limit its use for many clinical indications or applications.

Ultrasound imaging typically occurs within the near-field of a given aperture, which enables focusing on transmission, reception, or both. A challenging aspect of ultrasound imaging with large apertures is the high number of channel counts needed to address an aperture fully-populated with transducer elements, which increase with a square dependence on the aperture area in the case of a 2D aperture. Sparse apertures address this challenge by reducing the channel counts to a number that is cost-effective and practical. Sparse apertures may be combined with synthetic transmit aperture operation to extend the effective aperture size beyond its physical size, thus further reducing channel counts needed for operating a large aperture.

Synthetic aperture ultrasound imaging can be used to improve the quality of ultrasound images. A "synthetic aperture" is the concept in which the successive use of one or more smaller, real apertures (sub-apertures) to examine a volume-of-interest (VOI), whose phase centers are moved along a known one-dimensional (1D), two-dimensional (2D), and/or three-dimensional (3D) path of a particular or arbitrary shape, to realize a larger effective (non-real) aperture for acquiring an image. The synthetic aperture can be formed by mechanically altering the spatial position of the electro-acoustic transducer (e.g., transducer array) to the successive beam transmission and/or receiving locations, by electronically altering the phase center of the successive beam transmission and/or receiving locations on the electro-acoustic transducer array, or by a combination of any of above. Synthetic aperture-based imaging was originally used in radar systems to image large areas on the ground from aircraft scanning the area of interest from above.

Existing implementations of synthetic apertures in ultrasound imaging typically include mechanically scanning an aperture as described above, thereby precluding real-time operation and introducing a host of challenges. Electronic scanning of a synthetic aperture is far more desirable; however, the large number of elements required quickly become infeasible as the area of the effective aperture increases.

Synthetic aperture focusing in ultrasound imaging is based on the geometric distance from the ultrasound transmitting elements to the VOI location and the distance from that location back to the ultrasound receiving elements. In ultrasound imaging, the use of the synthetic aperture enables the focusing on a point in the target region by analyzing the received amplitude and phase data of the returned echoes (e.g., mono-static and bi-static echoes), recorded at each of a plurality of transmitter and receiver positions from all directions, to provide information about the entire area. Since the direction of the returned echoes cannot be determined from one receiver channel alone, many receiver channels are used to determine the information contained in the returning echoes, which are processed across some or all of the channels to ultimately render information used to produce the image of the target region.

A benefit of synthetic transmit aperture operation is that given an aperture of fixed size, the effective synthetic transmit aperture is twice the size. This concept is based on the principles of Fourier optics in the Fraunhofer approximation, where the far-field transmit-receive PSF of an aperture is based on the Fourier transform of the spatial convolution of the transmit aperture and the receive aperture. The doubling of the effective size of an aperture in synthetic transmit operation is well known. A sparse aperture operable in a synthetic transmit aperture mode can effective operate like an aperture of twice the physical size, or alternatively, given a fixed resolution PSF, a sparse aperture array operable in a synthetic transmit aperture model can be half the size of an equivalent non-sparse aperture. Such apertures are used in the disclosed embodiments.

Disclosed are systems, devices, and methods for sparse synthetic aperture ultrasound (SSAU) imaging and/or range-Doppler applications. In some embodiments, the SSAU disclosed systems and methods generate an optimized pair of mutually exclusive apertures that operate with multiple aperture openings such that the resulting point spread function is optimized for each combination of aperture openings and operable for focusing over multiple ranges and steering angles. In some embodiments, the optimization of a sparse aperture follows an algorithmic flow, which applies to optimization of any arbitrary type of sparse aperture constrained to any dimensionality, shape, or topology. In some implementations, the disclosed SSAU systems and methods can be used in acoustic imaging applications.

Example Optimizations for SSAU Imaging

FIG. 1 is a flow diagram of an algorithm for SSAU imaging optimization. As illustrated therein, the algorithm begins with defining the array topology, the array constraints, the objective space, and the objective function. Then, an acoustic field is pre-computed over the objective space for each array element, and the objective function is seeded (with a seed that satisfies the constraints) to initialize the optimization. An optimizer is used to minimize the objective function over the objective space, which results in the optimized array topology. The optimized array technology is then incorporated into the ultrasound imaging system.

Array topology. In some embodiments, the array can be configured as a 1D, 2D or 3D arrangement of transducer elements with defined positions and orientations in space. In an example, the arrangement can exist on a regular grid on a 1D line, a 2D plane or a 3D surface. In another example, the arrangement can exist arbitrarily in space.

According to embodiments of the disclosed technology, sparse aperture arrays can be defined in the aforementioned topologies. In an example, each of the sparse (or optimized) apertures include one or more of gaps, holes, voids, spaces, inactivated elements, deactivated elements, electrically switched off elements, and disconnected elements such that the aperture operates with transmit-receive spatial sampling similar to or more effectively than a full aperture, which does not include any gaps, holes, voids, etc. In another example, the PSF of the sparse apertures is functionally equivalent, if not more efficient and with better lobe characteristics than a fully sampled aperture occupying the same area, volume, or space.

Array constraints. In some embodiments, the array elements can be constrained to be either transmit-only, receive-only, or for both transmission and reception. In the example of non-overlapping, mutually exclusive transmit and receive sparse apertures, there is no need for a transmit-receive switch, e.g. a diplexer circuit, that protects receiver circuitry from high voltage transmissions and may isolate the receiver from transmitter noise. In other embodiments, some of the array elements can be constrained to operate together, e.g. elements that are electrically connected such that they operate effectively as a larger element. Herein, the electrical connection may be passive, active, or through an analog or digital beamformer on transmission and/or reception. In yet other embodiments, the constraint may be the maximum number of adjacent elements such that the area for signal routing and/or electronics is made available.

Objective space. In some embodiments, the objective space includes a sampled 3D field space adjacent to the array, e.g., a regularly-sampled, arbitrarily-sampled, functionally-sampled, analytically-sampled, or randomly-sampled volume in front of the array. In other embodiments, the objective space may consist of multiple objective spaces, e.g., if an array is used for multiple focal ranges and/or steering angles, it is typically preferable to sample the focal point or focal region and regions around the focus for each sub-space so as to accurately sample the diffracted fields. In yet other embodiments, the field can be sampled with at most one-half wavelength ($\lambda/2$) spatial sampling at the highest frequency component of the transmitted acoustic waveform.

Practical computational limitations may preclude the sampling to be less than one-half wavelength, in which case a smaller number of random samples may provide sufficient coverage to effectively sample the lobes. As ultrasound imaging occurs in the near-field of an array, it is preferable to sample the field within a radius extending from the geometric center of the array to the far-field transition of a fully-sampled aperture with an equivalent spatial extent, i.e., with gaps, holes, voids, and the like.

Objective function. In some embodiments, the objective function may include the maximum transmit-receive lobe level amplitude or power outside of a defined region of the main lobe. Lobes outside of the main lobe may be sidelobes, which are primarily due to coherent energy away from the main lobe and/or grating lobes, which are due to spatial aliasing of the main lobe and sidelobes when the beam is steered. In other embodiments, the objective function may include multiple steering and/or focal ranges that are evaluated separately, but are combined to generate a single scalar value using one or more linear operations (e.g., a simple or weighted average) and/or one or more non-linear operations (e.g., a logarithm operation).

In some embodiments, the objective function may optimize lobes for full transmit aperture operation, e.g. all transmit elements are active per a singular transmission event followed by a singular receive event on all receiver elements. In other embodiments, the objective function may optimize lobes for full transmit aperture operation, e.g. all transmit elements are active per a singular transmission event followed by a singular receive event on all receiver elements. In yet other embodiments, a 2D circular sparse aperture array may be optimized to have flat sidelobes instead of an Airy pattern of concentric rings around the main lobe caused by the Bessinc-squared diffraction typical of a full circular aperture. Similarly, a 2D square sparse aperture may be optimized to have flat sidelobes in the elevation and azimuth directions instead of typical sinc-squared diffraction patterns typical of a full square aperture. The sidelobe energy pushed down around the main lobe must be conserved and ends up in other locations less detrimental to imaging.

Pre-computing acoustic field. In some embodiments, the acoustic field for each element is precomputed using acoustic field simulation software based on linear and/or nonlinear acoustic wave propagation, which advantageously enables the efficient evaluation of the objective function for synthetic transmit aperture operation. Herein, it is assumed that transmitters and receivers obey reciprocity, e.g. transmitting on element 1 and receiving on element 2 is equivalent to transmitting on element 2 and receiving on element 1.

The transmitted acoustic waveform may be monochromatic, narrowband, or wideband. If a monochromatic simulation (e.g. Fresnel, Rayleigh-Sommerfeld, Fraunhofer, fast-nearfield, angular spectrum, 1D FFT, 2D FFT) is used to as a substitute for a computationally-expensive wideband simulation, the field is preferably simulated at the center frequency of the expected wideband transmit-receive response of the transducer. The transmit-receive response in the monochromatic case is the complex product of the transmit scalar field with the receive scalar field, which is far less computationally expensive than convolution of the transmit and receive responses in the time domain as required in a wideband simulation. Other wideband techniques may be used to simulate the acoustic field, e.g., the spatial impulse response method, evaluation of the Rayleigh-Sommerfeld integral in the time-domain, and summing evaluations of the Rayleigh-Sommerfeld integral at a set of discrete frequencies in the frequency-domain.

Seeding objective function. In some embodiments, locations of the elements can be randomly initialized as long as they are subject to the element location constraints. For example, the initial (or seed) values may be constrained by a number of nearest neighbors, maximum local density of elements, and/or allowed grouping orientations of multiple elements.

Minimizing objective function. In some embodiments, an optimization algorithm is used to minimize the objective function over the objective space subject to satisfying array constraints. In an example, the optimization algorithm selected may include one or more of simulated annealing, gradient descent, genetic algorithms, fractal-based techniques, etc.

Optimized array topology. The output of the workflow illustrated in FIG. 1 is an optimized aperture that satisfies the constraints (e.g., number of neighboring elements, number of transmit elements, number of receive elements, proximity of transmit elements relative to receive elements, symmetry of transmit elements, symmetry of receive elements) and design goals (e.g., maximum sidelobe level, maximum grating lobe level, steering range, focal range, aperture ratio of main lobe energy to lobe energy, PSF symmetry).

FIGS. 2-5 illustrate examples of 1D, 2D and 3D topologies for sparse aperture optimization. In some embodiments, array topologies (as illustrated, for example, in FIGS. 2 and 4) may include a plurality of polygon-shaped elements, e.g., plane elements with straight sides such as triangular, square, rectangular, pentagonal, hexagonal, heptagonal, octagonal elements, which may be characterized as convex, concave, simple, complex, or irregular.

In some embodiments, array topologies (as illustrated, for example, in FIGS. 3 and 4) may include a plurality of ellipsoidally-shaped elements, e.g., plane elements with closed curve sides such as ellipses and circles. These shapes may be found in transducer arrays fashioned from capacitive micromachined ultrasonic transducers (CMUTs), piezoelectric micromachined ultrasonic transducers (PMUTs), or poly vinylidene fluoride (PVDF) film.

In some embodiments, array topologies may include a plurality of arbitrarily-shaped elements. These shapes would be possible, for example, by micromachining a PVDF film or piezoelectric transducer (PZT) or by approximating the shapes using CMUT drums.

In some embodiments, array topologies may include 3D topologies such as geodesic topologies, triangulated topologies, polygonal topologies, and arbitrary topologies. In other embodiments, array topologies (as illustrated, for example, in FIG. 5) may lie on 3D surfaces such as spheres, cylinders, cones, ellipsoids, and parabolic surfaces.

In some embodiments, arbitrarily-shaped elements may be electronically selected within fully-populated arrays. In other embodiments, arbitrarily-shaped elements may be fixed within fully-populated arrays at the time of manufacture.

Figure 6:
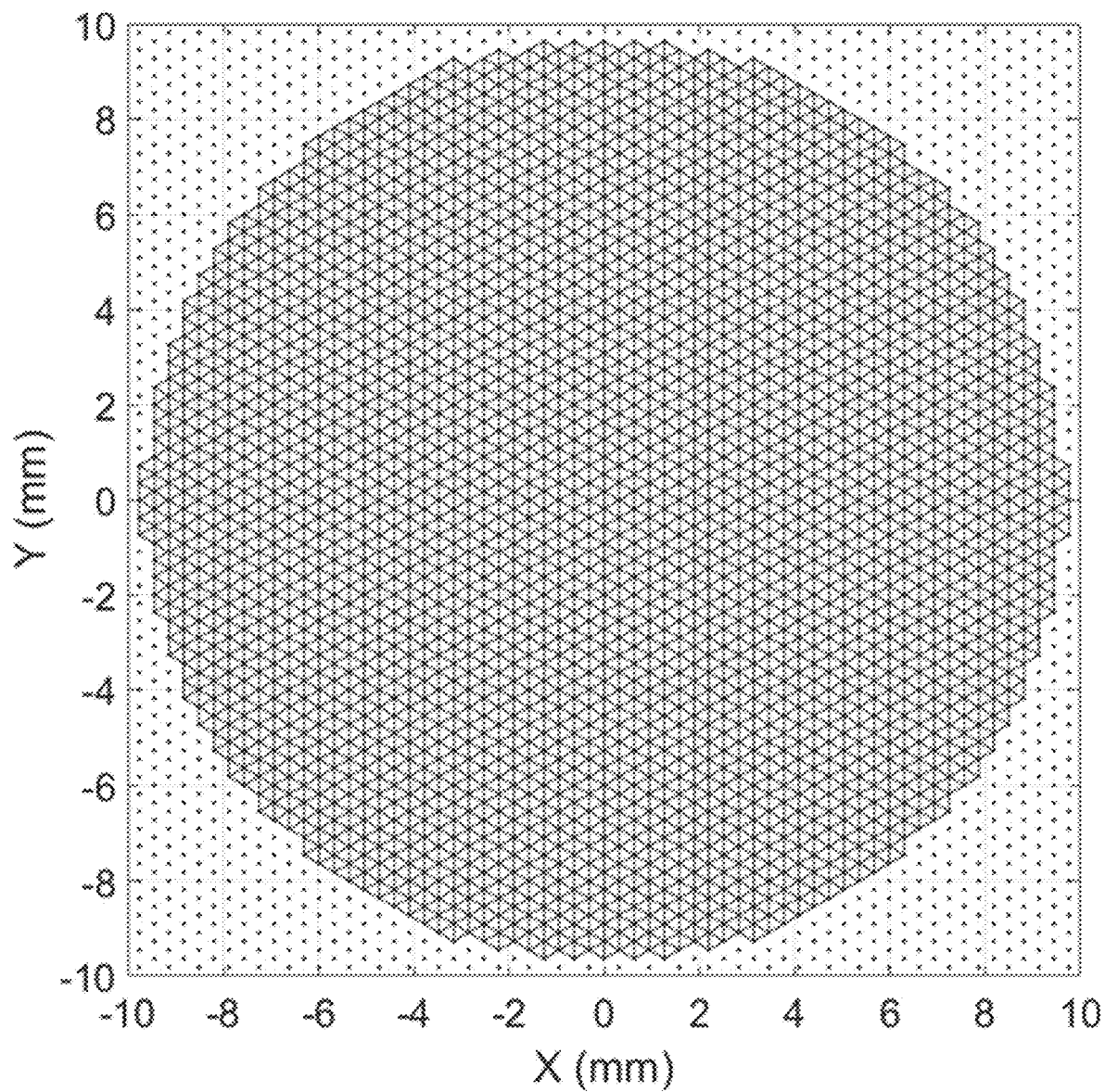
FIG. 6 illustrates an example of an optimization topology on a hexagonal grid.

FIG. 6 illustrates an example of an optimization topology on a hexagonal grid. In the example, the topology of the optimization problem starts with a 2D hexagonal grid defined by a pitch of 363.8 um centered at (0,0). Next, the grid is bounded by ±10 mm in the X and Y dimensions. The grid is further bounded by a circle of radius 9.8156 mm to include all possible drum centers contained within a 10 mm radius circle. The resulting grid is triangulated and non-equilateral triangles are rejected. The resulting set of equilateral triangles total 5090 possible three drum element locations. A set of rules is enforced to guarantee that elements do not overlap and each element has adjacent space for escape routing. A proprietary optimization algorithm is seeded based on the set of rules, and the optimal element locations for a given combination of $N_{TX}$ and $N_{RX}$ are determined. The objective of the optimization algorithm is to simultaneously optimize both sidelobes and grating lobes.

Overview of CMUT Technology

Capacitive micromachined ultrasonic transducer (CMUT) technology has enjoyed rapid development in the last decade. Advancements both in fabrication and integration, coupled with improved modelling, has enabled CMUTs to make their way into mainstream ultrasound imaging systems and find commercial success.

A CMUT includes a flexible top plate suspended over a gap. Transduction is achieved electrostatically, in contrast with piezoelectric transducers, for example, where transduction is achieved due to the piezoelectric effect. The merit of the CMUT derives from having a very large electric field in the cavity of the capacitor, a field of the order of $10^8$ V/m or higher results in an electro-mechanical coupling coefficient that competes with the best piezoelectric materials.

The availability of micro-electro-mechanical-systems (MEMS) technologies makes it possible to realize thin vacuum gaps where such high electric fields can be established with relatively low voltages. Thus, viable devices can be realized and even integrated directly on electronic circuits such as complimentary metal-oxide-semiconductor (CMOS). With respect to CMUT, an important development was the discovery of collapse mode operation of the CMUT. In this mode of operation, the CMUT cells are designed so that part of the top plate is in physical contact with the substrate, yet electrically isolated with a dielectric, during normal operation. The transmit and receive sensitivities of the CMUT are further enhanced, thus providing a superior solution for ultrasound transducers. In short, the CMUT is a high electric field device, and if one can control the high electric field from issues like charging and breakdown, then one can utilize the CMUT with superior bandwidth and sensitivity, amenable for integration with electronics, which can be manufactured using traditional integrated circuits fabrication technologies with all its advantages, and can be made flexible for wrapping around a cylinder or even over human tissue.

In ultrasound imaging systems, ultrasound probes typically do not contain any active electronics when the element count is low (e.g., <256), and all the front-end electronics is in the imaging system. For CMUT arrays, this poses a problem in the receive chain because of the typically high electrical input impedance of CMUT array elements. High input impedance combined with long cables result in loss of valuable signal-to-noise ratio (SNR) for the CMUTs. This problem is mitigated by including low noise amplifiers and/or buffers inside the probe, which amplify the signal before driving the cables. Even probes with piezoelectric transducers can benefit from using active electronics. When the element count is high such that the number of channels in the imaging system cannot match the number of elements in the array, the ultrasound probe will contain a certain amount of electronics that would take care of some of the front-end processing and reduce the number of transducer channels to match the number of channels in the imaging system. In this respect, CMUT technology has a distinctive advantage over piezoelectric transducer technology because of the variety of electronic integration possibilities it provides.

An integration option for CMUTs includes the monolithic integration of the CMUT array with the electronics in which the CMUT array is built on top of the electronic circuitry directly. Monolithic integration has always been considered the gold standard because of the compactness of the result and the elimination of extra integration steps associated with multi-chip approaches. However, this approach requires high volume production to be economically feasible, which is probably the reason why it did not find commercial traction until low cost, portable high volume ultrasound scanners became possible (e.g., Butterfly Network Inc., Guilford, Conn., USA). Whether a one-dimensional array or a two-dimensional array, monolithic integration provides a good interface (in terms of parasitics) between the CMUT array and the electronics. In monolithic integration, first the application specific integrated circuit (ASIC) is fabricated using a CMOS technology or similar, then the ASIC wafer is planarized using low temperature deposition and chemical-mechanical polishing (CMP) steps, which is followed by the CMUT fabrication using the sacrificial release process. There has been some success using a low-temperature bonding process for CMUT fabrication as well.

Multi-chip integration has been used to connect 2D CMUT arrays to the electronics. In this approach, the electronics and the CMUT array are built separately and brought together using a variety of integration options: flip-chip bonding with solder reflow, with gold stud bumps and anisotropic conductive films (ACF) or with thermo-compression bonding. These integration methods, though more practical to apply, are not unique to CMUTs and have been applied to piezoelectric matrix arrays with great success as well. For full 2D arrays where the number of individual connections is very high, fanning out interconnects to the sides where conventional interconnect schemes (e.g., wire bonding) can be used become impractical. In that case, flip-chip bonding the 2D CMUT array onto the electronics was used. The amount of electronic integration that can be incorporated into a CMUT probe varies depending on many parameters, ranging from size to power consumption to the type of application.

CMUTs for ultrasound imaging applications have primarily been developed for operation above 2 MHz center frequency primarily due the higher demand at clinically relevant frequencies. Low-frequency CMUTs in the 0.5-1 MHz frequency range have been developed primarily for therapeutic ultrasound applications. Yet, a primary challenge for developing low-frequency CMUTs is managing mechanical stresses for a given drum size and thickness needed for 1 MHz resonance. Since CMUTs have great bandwidth capabilities, an alternative approach is to suitably drive a higher-frequency design such that a 1 MHz center-frequency output is produced.

In some embodiments of the disclosed sparse synthetic aperture ultrasound systems, devices and methods, CMUTs can be used in an acoustic coupling device that couples to a body part of a subject for transmitting and receiving acoustic signals at/from a target volume, in which the CMUT acoustic coupling device can be used in an acoustic imaging system. Example embodiments and implementations of acoustic imaging systems, devices and methods capable of implementing the disclosed Sparse Synthetic Aperture Ultrasound imaging techniques are described below and U.S. Pat. No. 9,844,359, which incorporated by reference as part of the disclosure in this patent document.

Example Acoustic Imaging System Using CMUT Segment

In some embodiments, an acoustic imaging system includes an acoustic coupling device that provides CMUT array segment that can augment or substitute for piezoelectric transducer array. For example, in prior experiments, a system that includes a 11×11 2D piezoelectric transducer (PZT) array operating at a nominal center frequency of 0.9 MHz with a −6 dB two-way fractional bandwidth of 60% suffered some problems with the PZT design, such as large physical size (primarily in the thickness dimension, perpendicular to the array face), unfocused operation, and cost. To address such challenges, some primary design requirements of the CMUT array include, for example, 1 MHz center frequency of operation, 70% or more fractional bandwidth (−6 dB two-way), <=1 cm thickness (including support structure, electronics, and cabling), aperture size of 2.5 cm enabling focused operation out to 10 cm in depth, <=128 receive (RX) channels/elements, and <=512 transmit (TX) channels/elements. For example, the volume production cost of CMUT is at least two orders of magnitude lower than PZT (excluding NRE).

In this example, a transition from PZT to CMUT involves several changes to the physical array and its acoustic performance. The primary physical changes include a >500% thinner profile (e.g., from 5 cm to <1 cm) and a 200% larger aperture (e.g., from 1 cm to 2 cm). The thinner profile results in significantly less mass and more freedom to place segments on certain portions of a subject's body, e.g., such as leg body parts including the posterior side of the femur and tibia, e.g., as compared to the obstructive dimensions of the PZT array. Unlike PZT, for example, the low profile of the CMUT array allows complete 360 degree coverage of spatial samples around the subject's body parts, e.g., such as the leg bones during full flexion of knee. In other words, gaps that were needed for the PZT array can either be reduced (e.g. from 60 degrees to 30 degrees) or avoided altogether.

The relatively low cost of the CMUT array allows for a larger aperture, which extends depth over which the acoustic beam may be focused. The Fresnel distance, or the distance at which an unfocused aperture transitions from near-field to far-field, approximately defines the maximum distance at which beam focusing may be achieved. The Fresnel distance is for a circular disk aperture is approximated by the following equation:

$$D_f = \frac{d^2}{4\lambda},$$

where d is the aperture diameter and $\lambda$ is the acoustic wavelength assuming a soft tissue sound speed of 1540 m/s. In this example, the current PZT design operates at 0.9 MHz center frequency and has a 1 cm diameter aperture, which results in a Fresnel distance of about 1.46 cm. Thus, the PZT array is primarily operated with no focusing, only steering.

In comparison, the example acoustic coupling device with a 1 MHz CMUT design includes a 2.5 cm diameter aperture with a Fresnel distance of 10 cm. The larger aperture size limits the placement of adjacent segments; however, simplifications in cabling due to electronics integration within the ASIC compensate for the increased size of the aperture compared with the example PZT acoustic coupling device.

In an example, a 2.5 cm diameter aperture with $\lambda/2$ pitch required of phased array steering requires at least 32×32 elements at 1 MHz (c=1540 m/s throughout). As RX channels are expensive due to cost of analog-to-digital converters (ADCs), it is cost-prohibitive to fully populate the array with 1024 RX channels. One solution to this problem is to operate the CMUT array as a sparse aperture array. In the Fraunhoffer limit, the far field TX/RX point-spread-function response of an aperture is the 2D Fourier transform of the spatial convolution of the TX and RX apertures, it is possible to sparsify both the TX and RX apertures to obtain a virtually equivalent spatial sampling as compared to fully-populated apertures.

In some implementations, for example, the sparse apertures are fixed and not reconfigurable. Therefore, a sparse aperture that works well at 10 cm depth at f/4 may not work equivalently at 5 cm depth at f/4 due to the fact that the TX/RX sparse array needs to have a smaller 1.25 cm aperture. Not all sparse aperture types are limited in this way, but they generally compromise performance in SLL and GLL to be operable at multiple depths at a constant f-number. Another option, for example, is to employ several different sparse apertures optimized for different depths. Yet, in examples discussed below, one optimized sparse is used as it is believed to be the most economical and patient-adaptable route.

Example Sparse Apertures for Acoustic Imaging

Example embodiments and implementations are described for sparse apertures operable at multiple focal depths, steering angles, and aperture openings, similar to multifocal intraocular lenses, e.g., for near-range, mid-range, and far-range focusing. In some examples described herein, primarily to simplify electronics (and reduce NRE cost), the constraint of non-overlapping TX/RX sparse apertures is explored.

In some embodiments, an example system includes a 2D array of transducers operable such that a set of elements is used only for transmission and a separate and exclusive set is used only for reception. In some examples, the total number of elements used for transmission and reception is less than the total number of elements in the aperture, e.g. for 1024 elements comprising a 32×32 array, 128 elements are used for transmission and 128 elements are used for reception. Yet, in some examples, the number of elements used for reception is much less than the number of elements for transmission, e.g., 512 elements for transmission and 128 elements for reception. In one example embodiment, the set of sparse apertures is optimized for minimum side lobe level for two sparse aperture openings and operable for three combinations of said aperture openings, e.g. half aperture transmission, half aperture reception for near-range focusing; half aperture transmission, full aperture reception for mid-range focusing; and full aperture transmission and full aperture reception for far-range focusing.

In some embodiments, an example of a high-level CMUT segment includes one or more of the following design parameters and optimization constraints:
- Center frequency of 1 MHz;
- −6 dB two-way fractional bandwidth of 80%;
- Steering to ±45 degrees in both azimuth and elevation;
- Focused operation from 2-10 cm;
- Aperture size 25 mm (32 mm segment-to-segment spacing);
- ≤128 RX elements/channels;
- ≤512 TX elements/channels;
- Non-overlapping TX and RX elements;
- Multi-focal operation (i.e. near, mid, far);
- Octant symmetry; and/or
- Lobes ≤−30 dB across all steering and focusing ranges.

In some example embodiments of the CMUT-employed acoustic imaging system, non-apodized, mutually-exclusive binary TX and RX sparse apertures are explored. The search space for two complementary binary masks defining a TX and a RX aperture pair is enormous, but it is possible to reduce the size of the space by limiting the number of unique permutations. Some embodiments disclosed herein are limited to circular disk masks, e.g., due to the isotropic nature of the circular disk aperture PSF (e.g., Airy pattern) compared with the square aperture PSF. Also, for example, some of the embodiments described below are limited to only those masks with octant symmetry. Octant symmetry is equivalent to transpose symmetry for each quadrant, which results in transpose symmetry for the entire mask.

Figure 7:
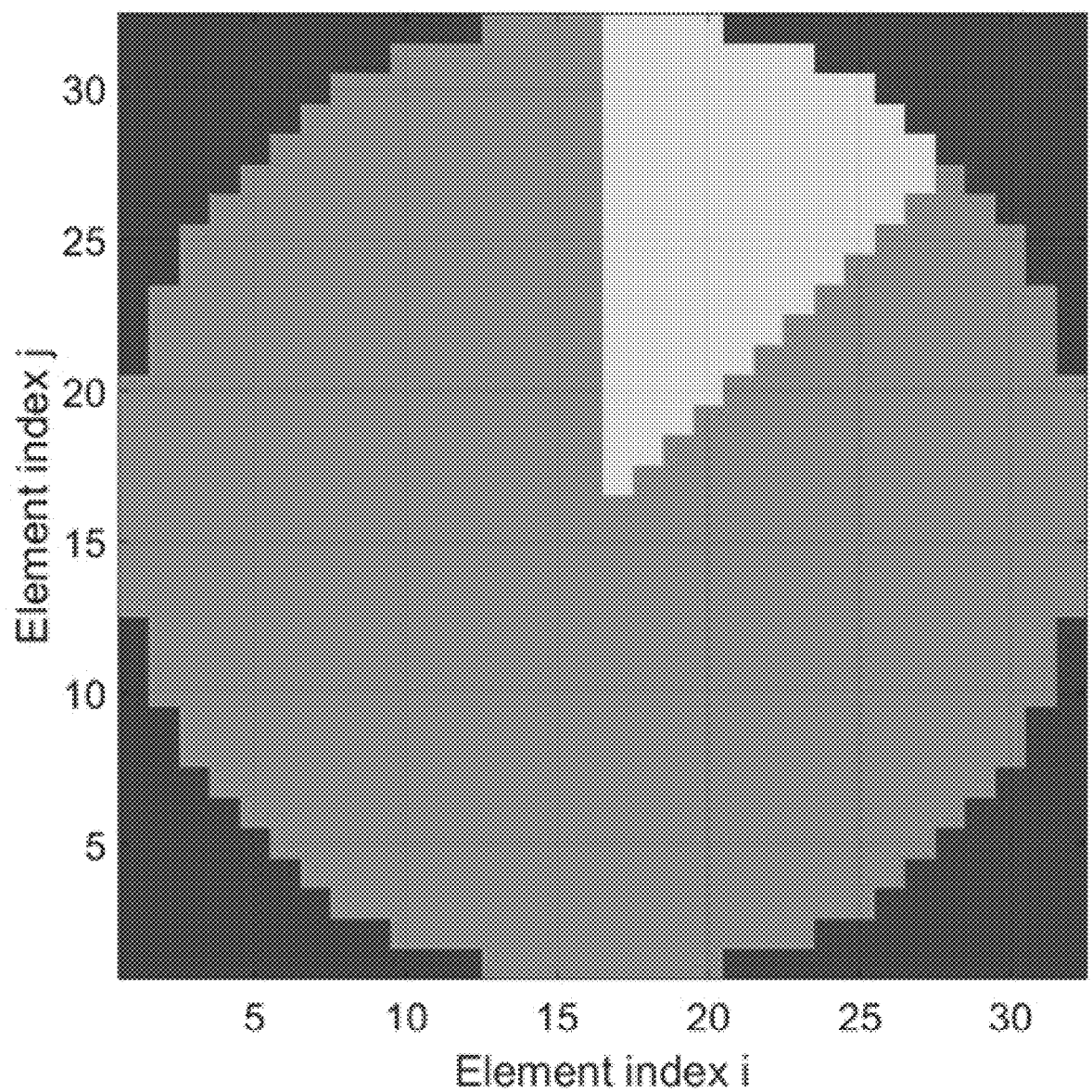
FIG. 7 is a diagram illustrating an example 32×32 mask showing a fully populated circular aperture containing 812 total elements with an octant of 107 elements.

FIG. 7 depicts an example 32×32 aperture topology or mask with row index i spanning 1 . . . 32 and column index j spanning 1 . . . 32. The portions in yellow and green comprise a circular disk aperture containing 812 elements. The yellow octant of the disk contains 107 elements, which get replicated as necessary to fill the entire aperture. For this octant, the equivalent integer value for all 107 binary values set to one is 81129638414606681695789005144063 or 8.11e31 (!). Many values in this range are poor choices, but the sheer number of possibilities all but guarantees that some are better than others and that some are very good. This space is searched by randomly generating binary TX and RX masks subject to constraints of octant symmetry, mutual exclusivity, number of TX elements, and number of RX elements. The search is guided by a simulated annealing algorithm. Each candidate set of masks is zero-padded to 128×128, the two-way far-field PSF is computed using the 2D Fast Fourier Transform (FFT), and the SLLs are quantified outside of the main lobe. For a given number of TX elements and RX elements returned by the optimizer, the set of patterns with the best SLLs are stored. In order to satisfy octant symmetry together with arbitrary randomized element selection over the octant, the number of elements is allowed to vary up to the desired number. For example, if 128 TX and 128 RX elements are requested, the optimizer may return a pair of optimized masks with 124 TX and 120 RX elements. For even N, optimized mask contain element counts that are a multiple of 4 due to the fact that a quadrant is obtained with a logical OR operation between the octant and its transpose; thus, the diagonal elements are counted only once in the element count per quadrant (hence multiples of 4).

The optimized apertures presented herein represent what can be achieved after a non-exhaustive search (for these example implementations), and does not preclude the existence of special or ideal patterns. In these example implementations, sparse aperture optimization was performed in MATLAB, and would benefit from translation to a compiled language such as C++. The analysis here is simplified considerably to make it a tractable problem; however, several techniques may be employed to further improve the performance of sparse apertures, which include optimization of RX apodization, use of virtual elements, use of different element shapes, optimizing element directivity, and array thinning.

Figure 8:
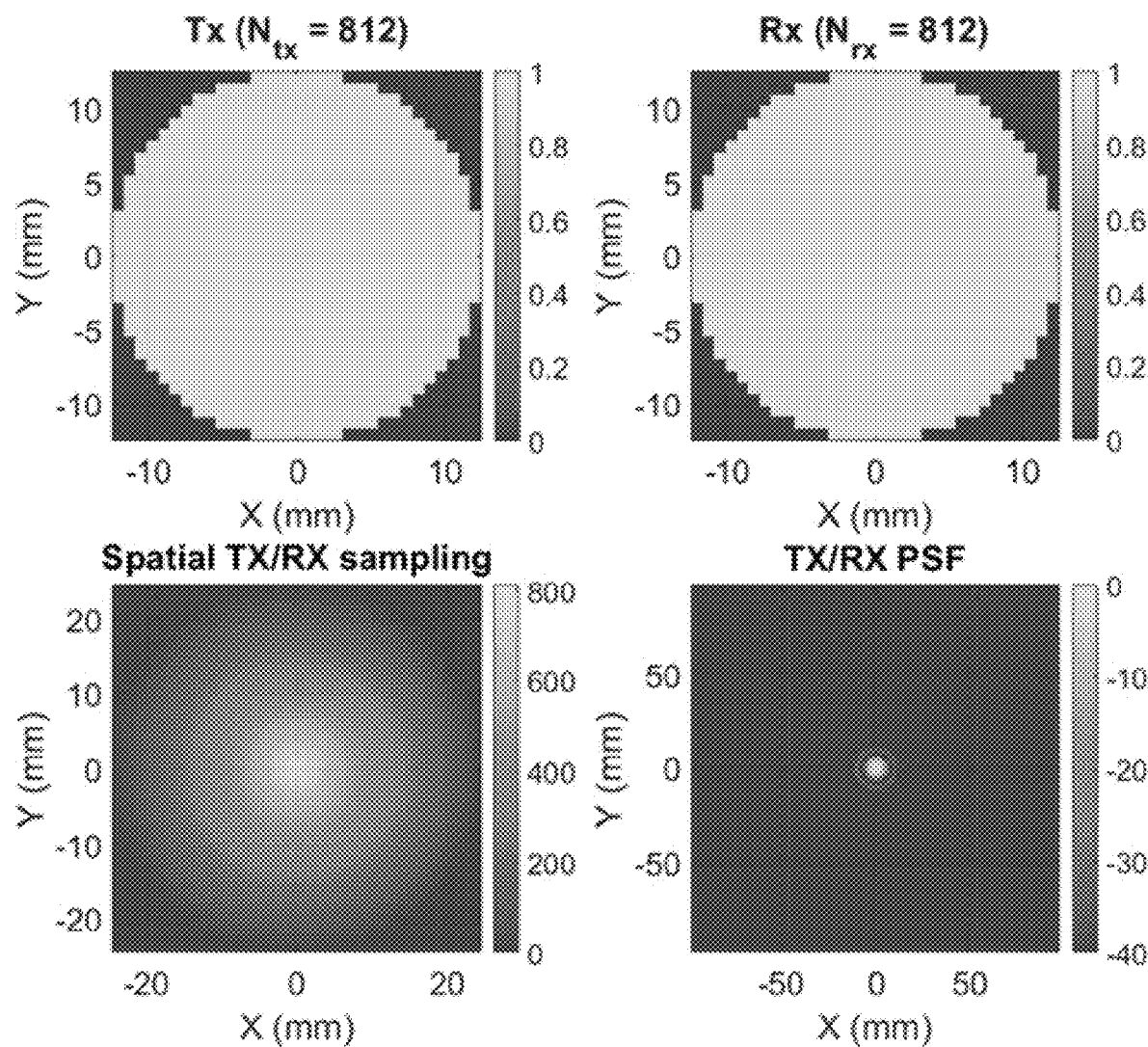
FIG. 8 illustrates an example of ideal transmit (TX) and receive (RX) apertures and the corresponding TX/RX spatial sampling point spread functions (PSF).

FIG. 8 shows diagrams of example ideal TX and RX apertures (top left and top right) and corresponding TX/RX spatial sampling PSF (bottom left and bottom right). Here the SLL<=−35 dB and $E_{ML2SL}$=26.4 dB ($E_{ML2SL}$ is the ratio of the main lobe energy to the side lobe energy in dB). For the apertures, yellow is active, blue is inactive. For the diagrams shown in FIG. 8, the TX/RX spatial sampling and PSF magnitude was obtained from the set of ideal binary 32×32 circular disk TX and RX apertures. All axes are in units of mm. The TX/RX PSFs are sampled at $\lambda/2$ resolution assuming $\lambda$=1.54 mm and a focal plane at 100 mm. The diameter of the PSF to the first zero crossing occurs is 11 samples (8.5 mm), in close agreement with the expected value of 10.76 (8.3 mm). Note that the effective TX/RX aperture is twice the size of the individual TX and RX apertures. The magnitude of the two-way far-field PSF is normalized and plotted on a log scale ranging from −40 dB to 0 dB. Note the first side-lobe is visible as a ring around the main lobe and peaks at the −35 dB level. The ratio of the energy in the main lobe to the energy in the sidelobes is 26.4 dB.

Figure 9:
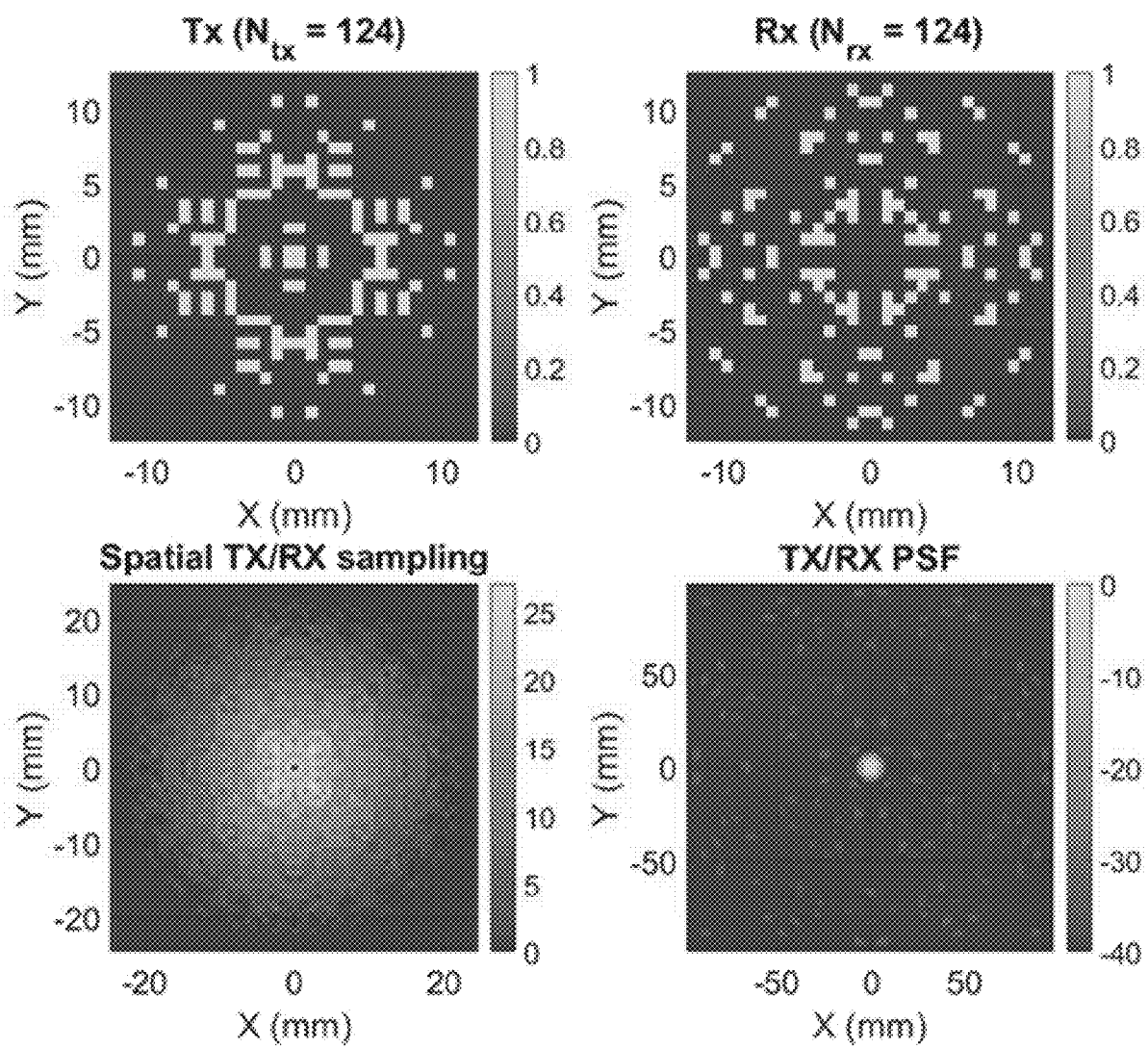
FIG. 9 illustrates an example of optimized TX and RX sparse apertures and the corresponding TX/RX spatial sampling PSF.

FIG. 9 shows diagrams depicting example optimized TX and RX sparse apertures (top left and top right) and corresponding TX/RX spatial sampling PSF (bottom left and bottom right). Here the SLL<=−35 dB and EML2SL=14.6 dB. For the apertures, yellow is active, blue is inactive. FIG. 9 shows a contrasting example for an optimized set of sparse TX and RX 32×32 apertures consisting of 124 TX elements and 124 RX elements (up to 128 TX and 128 RX elements were requested of the optimizer). Note the optimized apertures have a combined spatial sampling that approximates that of the ideal case, and that the PSF largely approximates the PSF of the ideal case, with sidelobe levels also at or below the −35 dB level.

One example impact of SLL optimized sparse apertures is in the ratio of the energy in the main lobe to the sidelobes, denoted as $E_{ML2SL}$, which is 14.6 dB for this particular set of sparse apertures compared to 26.4 dB in the ideal case. The goal of the optimizer is to distribute this sidelobe energy as uniformly as possible over space. For example, the disclosed SSAU imaging systems, devices, and methods are able to interrogate soft tissue in body parts that include bone, which create difficulties in imaging using ultrasound. From the viewpoint of normal specular scattering from bone targets, this sidelobe and grating lobe energy is largely scattered away from the direction of the main lobe when the main lobe is steered and focused normal to a reflector, thus lobe energy is practically negligible regardless of its amplitude. For example, this is primarily a consequence of the law of reflection, e.g., angle of reflection equals the angle of incidence combined with the geometry of long bones (e.g., tibias and femurs). Lobe levels below −40 dB are practically negligible for the application of detecting very strong specular bone reflections since the Rayleigh scattering in soft tissue at 1 MHz is at least another −40 dB down compared with bone based on the power law frequency dependence of skeletal muscle of about 0.53 vs. 3.26 for calcaneus bone.

Table 1 shows example optimized TX/RX sparse apertures showing element counts and sidelobe levels. The best values are bolded.

TABLE 1

| TX/RX pair identifier number | N | $N_{tx}$ nom | $N_{rx}$ nom | $N_{tx}$ opt | $N_{rx}$ opt | $N_{tx}$ half | $N_{rx}$ half | $E_{ML2SL}$ Far (dB) | SLL Near (dB) | SLL Mid (dB) | SLL Far (dB) |
|---|---|---|---|---|---|---|---|---|---|---|---|
| 1  | 32 | 128 | 64  | 120 | 60  | 120 | 32 | 15.41 | 30.08 | 33.94 | 33.94 |
| 2  | 32 | 128 | 128 | 120 | 116 | 112 | 32 | 15.81 | 31.42 | 35.39 | 35.60 |
| 3  | 32 | 256 | 64  | 244 | 52  | 148 | 32 | 15.97 | 32.28 | 34.64 | 35.22 |
| 4  | 32 | 256 | 128 | 240 | 120 | 140 | 32 | 18.09 | 32.80 | 35.91 | 38.89 |
| 5  | 32 | 512 | 64  | 484 | 64  | 168 | 32 | 18.71 | 31.53 | 35.86 | 39.89 |
| 6  | 32 | 512 | 128 | 480 | 120 | 168 | 32 | 20.58 | 32.97 | 38.44 | 41.75 |
| 7  | 33 | 128 | 64  | 96  | 64  | 92  | 32 | 10.94 | 28.83 | 30.78 | 30.15 |
| 8  | 33 | 128 | 128 | 120 | 116 | 104 | 32 | 15.52 | 29.14 | 34.71 | 35.81 |
| 9  | 33 | 256 | 64  | 213 | 64  | 129 | 32 | 14.24 | 31.20 | 32.65 | 33.91 |
| 10 | 33 | 256 | 128 | 225 | 112 | 133 | 32 | 16.65 | 31.45 | 35.94 | 37.16 |
| 11 | 33 | 512 | 64  | 457 | 60  | 153 | 32 | 18.16 | 32.44 | 33.16 | 39.98 |
| 12 | 33 | 512 | 128 | 449 | 116 | 173 | 32 | 19.79 | 33.35 | 37.98 | 41.09 |

Figure 10:
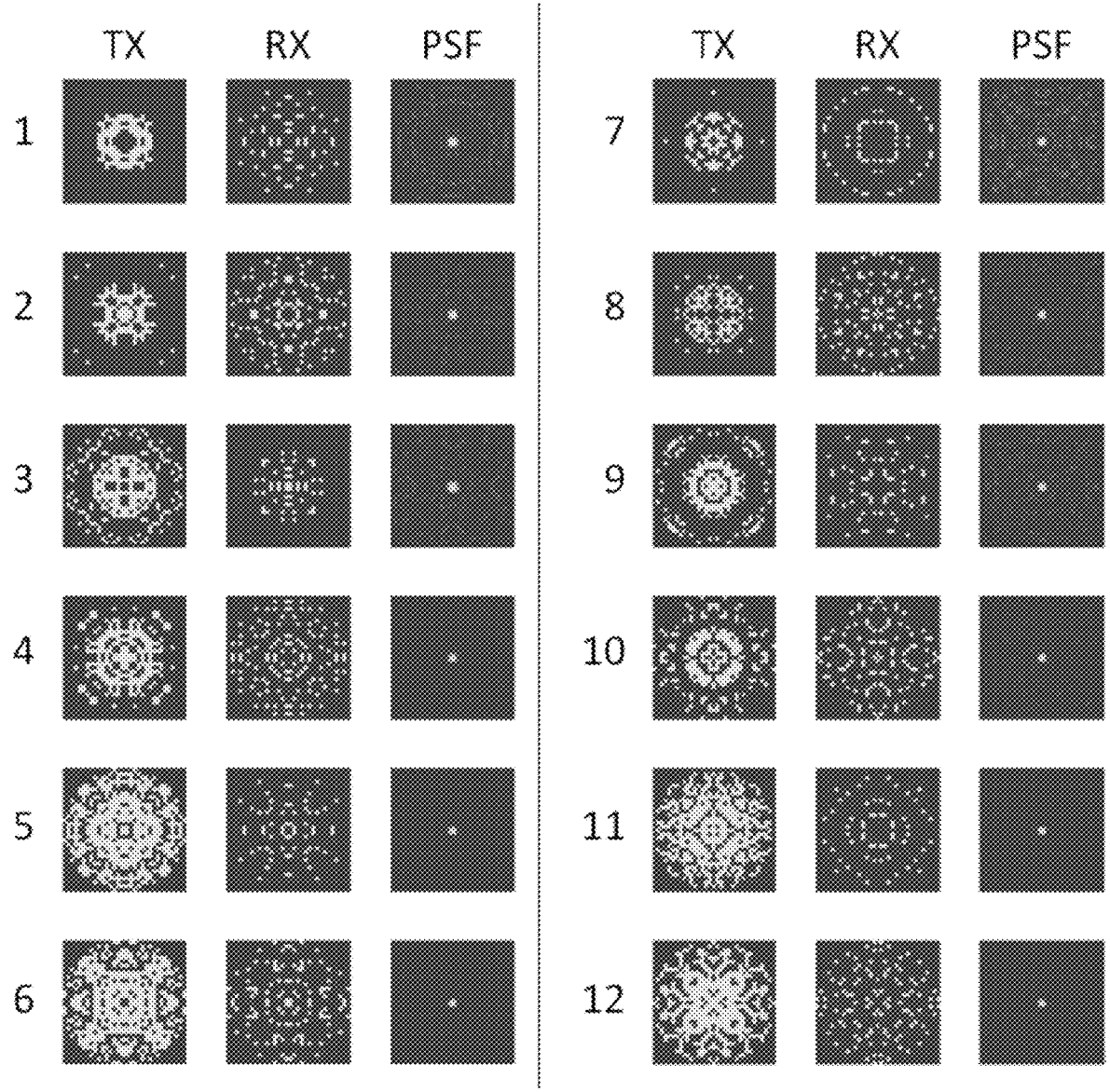
FIG. 10 illustrates an example of optimized apertures in the far field.

Several sets of TX/RX sparse apertures have been optimized for the example cases shown in Table 1. The corresponding optimized apertures and the far-field PSFs are shown in FIG. 10. The optimized SLLs for each TX/RX pair for each of the three focusing ranges are shown in three rightmost columns of Table 1. In general, more TX and RX elements result in lower SLLs and higher $E_{ML2SL}$ in most cases (e.g., 128 RX is better than 64 RX). Across all cases, the clear winners are pairs 6 and 12. Pairs 5 and 11 are excellent alternatives with nearly equivalent SLLs and require only 64 RX channels. Pairs 3 and 9 are very good choices as well, especially if SLLs can be improved with various digital beamforming techniques. Note that an additional constraint of 32 elements was added for the half-aperture RX mask for both the 32×32 and 33×33 arrays. This constraint was necessary because some optimal patterns required very few half aperture RX elements (e.g., 8 or 16), which is not desirable due to loss of beamforming SNR. There is not a clear advantage to having an odd number of elements except for the fact that an element may be present at the geometrical center of the array, which often serves as the phase center in beamformation, and is not a necessary condition for proper beamforming.

FIG. 10 shows diagrams of example optimized apertures in the far field. The left set of diagrams shows TX (left column) and RX (middle column) sparse aperture pairs for the first 6 optimized cases in Table 1 (32×32). Yellow is active, blue is inactive. Normalized full aperture far field PSFs (right column) for each pair are shown on a 40 dB scale. The right set of diagrams shows TX (left column) and RX (middle column) sparse aperture pairs for optimized cases 7-12 in Table 1 (33×33). Yellow is active, blue is inactive. Normalized full aperture far field PSFs (right column) for each pair are shown on a 40 dB scale.

To investigate the wideband acoustic performance of the optimized apertures, example simulations were performed using a linear acoustic field simulator (running in MATLAB) that is based on the spatial impulse response method for computing fields generated from rectangular sources, which makes it flexible for studying fields generated using arbitrary responses on both transmit and receive.

In the example simulations, an overall aperture size of 25 mm×25 mm is assumed. Additionally, square elements are assumed with a spacing between elements or kerf of 0.03 mm. The grid dimension of the aperture is given by N, (e.g. N=32 for a 32×32 aperture).

To find the width of a square element, W, the following equation is used:

$$W = \frac{D - K(N-1)}{N},$$

where D is the diameter of the aperture, K is the kerf, and N is the grid dimension.

To find the spacing between elements or pitch, P, the following equation is used:

$$P = K + W.$$

Applying values of D=25 mm, K=0.03 mm, and N=32 result in an element width of 0.752 mm (0.49λ) and a pitch of 0.782 mm (0.508λ) at 1 MHz, which is very close to the desired pitch of 0.77 mm or λ/2 (c=1540 m/s). For higher values of N, the pitch is obviously reduced; however, at the expense of a smaller active aperture area for a fix number of TX or RX elements. Reduced pitch is beneficial for reducing grating lobe components due to frequency components in the transmitted pulse that are higher than the nominal frequency of 1 MHz. In the linear acoustic field simulation, each square element is subdivided into 2×2 mathematical elements for more accurate field generation.

In these examples, the impulse response of the CMUT can be modeled as a "t-cubed" pulse given by the following equation:

$$p(t) = A_0 t^3 e^{-Bt} \sin(2\pi f_0 t),$$

where t is time, $A_0$ is the amplitude, B is an exponential decay term, and $f_0$ is the center frequency.

Figure 11:
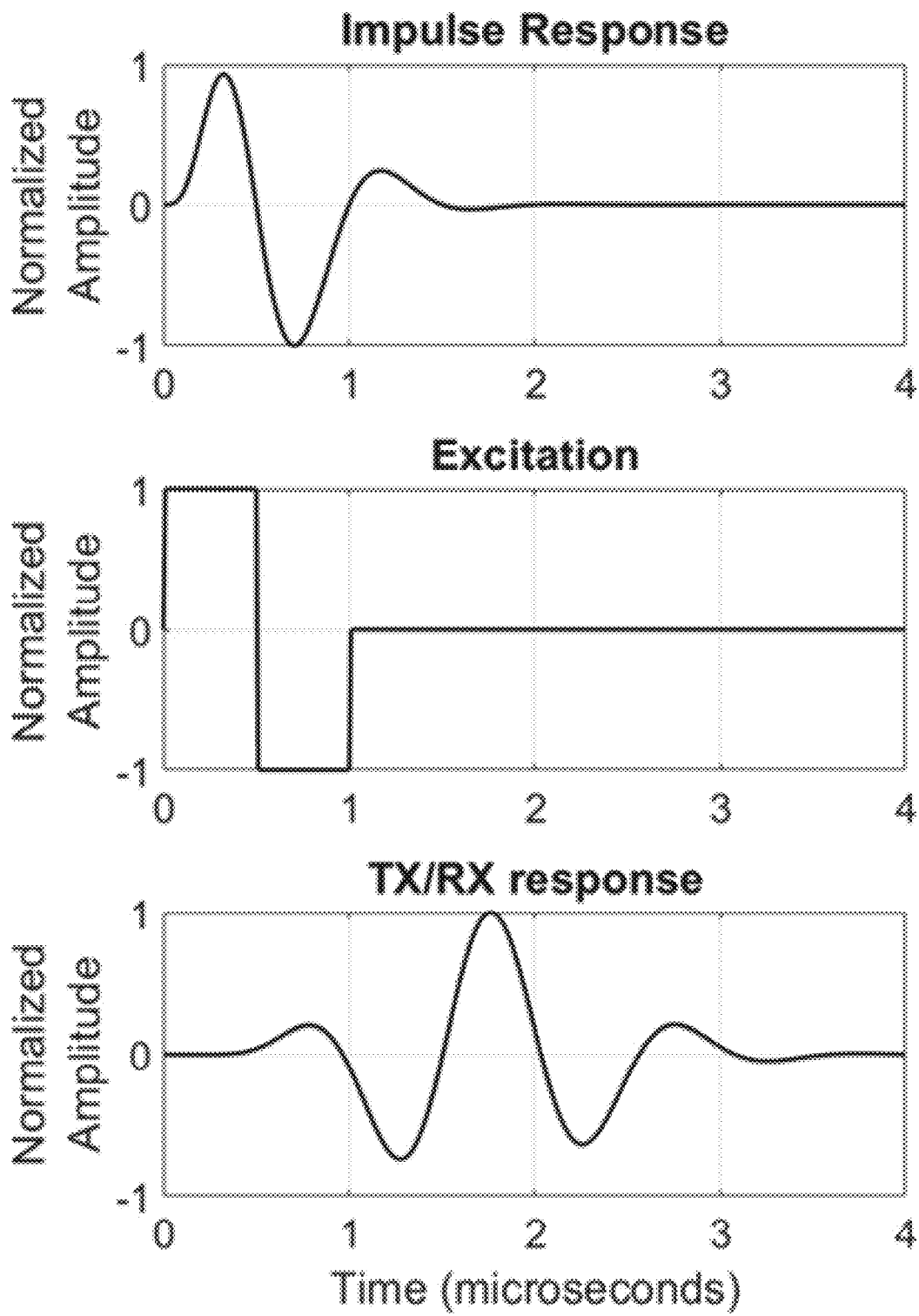
FIG. 11 illustrates examples of an impulse response, an excitation pulse, and a TX/RX response used in linear acoustic field simulations.

FIG. 11 shows diagrams showing example impulse response (top), excitation pulse (middle), and TX/RX response (bottom) used in the linear acoustic field simulations. (Top) The one-way −3 dB impulse response is 80% fractional bandwidth at 1 MHz center frequency. (Middle) The excitation is a 1 cycle square wave at 1 MHz center frequency. (Bottom) The TX/RX response has 65% fractional bandwidth centered at 1 MHz center frequency.

For all linear acoustic field simulations, B was chosen to be 6.13e6 s$^{-1}$, which yields a −3 dB one-way fractional bandwidth of 80% shown in FIG. 11 (top). $A_0$ was chosen to normalize the one-way response. To simulate the digital excitation, a single-cycle bipolar square wave was used, as shown in FIG. 11 (middle). The resulting two-way −6 dB fractional bandwidth of the impulse response and excitation pulse is a conservative value of 65%, also shown in FIG. 11 (bottom). Choice of a different excitation pulse could improve bandwidth, e.g. a half-cycle pulse; however, the capability of the CMUT in this low frequency range is unknown, and a conservative value for bandwidth was determined to be prudent for these example implementations.

Figure 12:
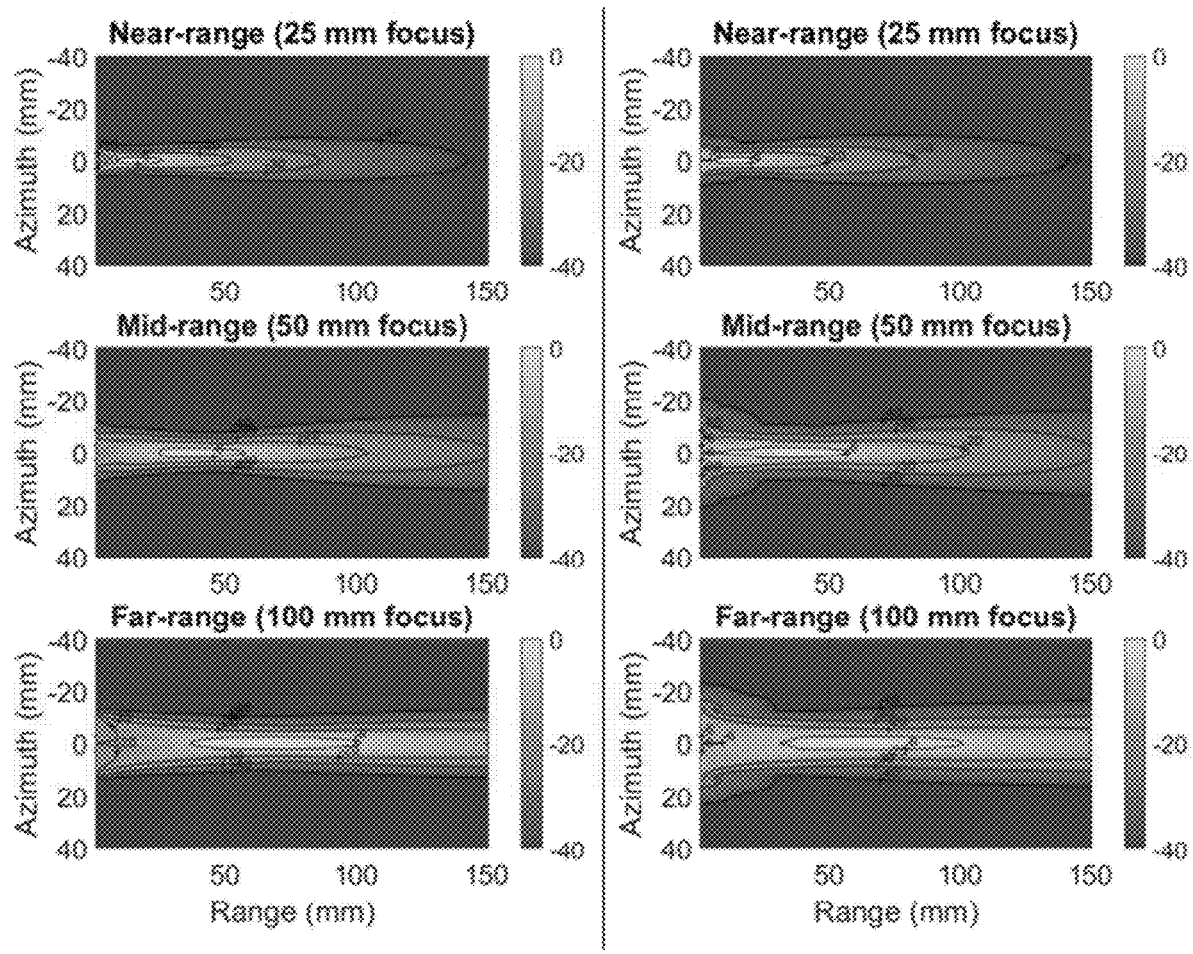
FIG. 12 illustrates examples of normalized on-axis (no steering) beam plots of three sets of TX/RX aperture sizes.

FIG. 12 shows diagrams depicting example normalized on-axis (no steering) beam plots of the three sets of TX/RX aperture sizes investigated. The example plots of FIG. 12 were generated in the linear acoustic field simulation. On the left, the apertures are full and not sparse; on the right, the apertures are sparse with 484 TX and 128 RX full aperture elements and 156 TX and 32 RX half aperture elements. The top plots show half diameter RX and half diameter TX for near-range operation out to 25 mm, the middle plots show half diameter TX and full diameter RX for mid-range operation out to 50 mm, and the bottom plots show the full TX and full RX aperture for long-range operation out to 100 mm.

Example on-axis beam plots of the three different cases are shown in FIG. 12 for full apertures (left) and sparse apertures (right) and near-range (top), mid-range (middle), and far-range (bottom) cases. The sparse aperture counterparts are generated using an optimized aperture with 484 TX elements and 128 RX elements. The optimized SLLs for each case, i.e. near, mid, and far, are −29.9 dB, −37.4 dB, and −42.5 dB, respectively. Note that the −6 dB working depths for each case are similar between the full and sparse apertures, and the working depths overlap between all three cases. The approximate working ranges of all three cases are 1.25-3.0 cm, 2.4-6.0 cm, and 5.0-11.0 cm.

Figure 13:
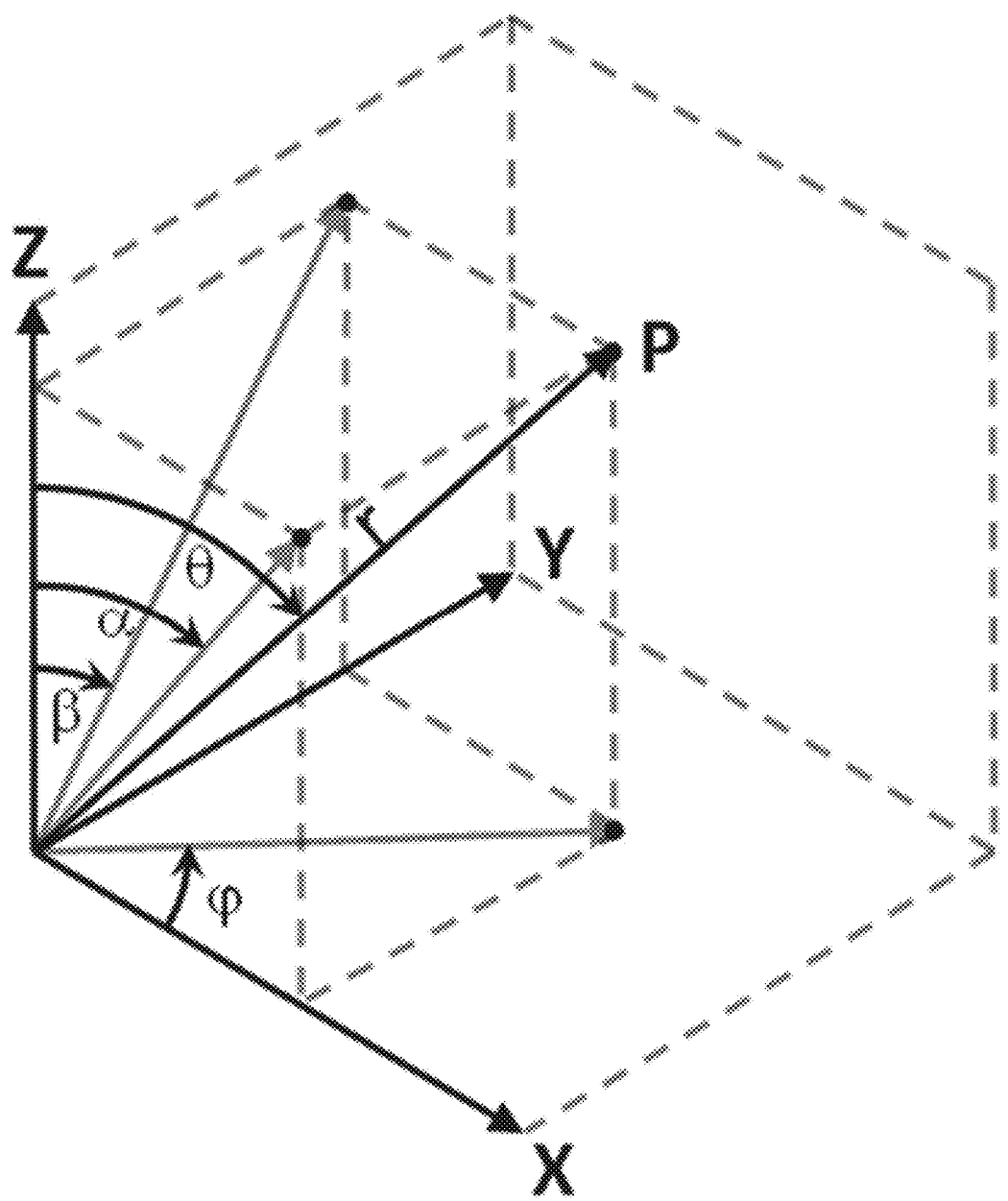
FIG. 13 illustrates an example coordinate system used in the linear acoustic field simulations.

FIG. 13 shows a diagram of an example coordinate system used in the linear acoustic field simulations. Field point P and its corresponding vector may be represented in ISO spherical coordinate system as (r, θ, φ), where r is the scalar distance, θ is the polar angle between the X axis and the projection of P onto the XY plane, and φ is the ISO azimuthal angle from the Z axis to vector P. Point P may also be represented as (r, α, β), where α is the angle from the Z axis to the projection of P onto the XZ plane, and β is the angle from the Z axis to the projection of P onto the YZ plane. Herein, the angle α is referred to as azimuth, and the angle β is referred to as elevation. The array segment lies in the XY plane and positive Z is front of the array. When steering in azimuth only, the beam is in the XZ plane. When steering in elevation only, the beam is in the YZ plane.

The grating lobe performance of the optimized sparse apertures is studied using the linear acoustic field simulation, and using the coordinate systems shown in FIG. 13. Firstly, the ISO spherical coordinates (r, θ, φ) are shown for a field point, P. Secondly, the field point P may also be represented using the coordinates (r, α, β) as described in the figure caption. To be consistent with definitions of azimuth and elevation used in medical ultrasound imaging, the angles α and β are herein referred to as azimuth and elevation, respectively. For example, steering only in azimuth from −90 degrees to 90 degrees is limited to the positive Z direction within the XZ plane. Likewise, steering only in elevation from −90 degrees to 90 degrees also limited to the positive Z direction, but in the YZ plane. Steering in both azimuth and elevation over −90 to 90 degrees at a constant range, r, is limited to the positive Z hemisphere. The Cartesian coordinates on the hemisphere may be found directly from (r, α, β) using the following set of equations:

$$z = \pm \frac{r}{\sqrt{1 + \tan^2\alpha + \tan^2\beta}}$$
$$x = z\tan\alpha$$
$$y = z\tan\beta$$

Sampling the hemisphere using a regular grid over α and β results in a non-uniform sampling over the hemisphere particularly near ±90 degrees. More uniform samples over the hemisphere are obtained using a variant of Vogel's method based on the golden angle (derived from the golden ratio) applied to a sphere, which essentially samples the hemisphere using an optimal spiral. An example hemispherical sampling is shown in FIG. 12 for a radius of 10 cm. A maximum nearest-neighbor sampling distance of 0.7 mm (<λ/2) requires 19,905, 77,310, 304,620 points for a 2.5 cm, 5.0 cm, and 10 cm hemisphere, respectively.

Figure 14:
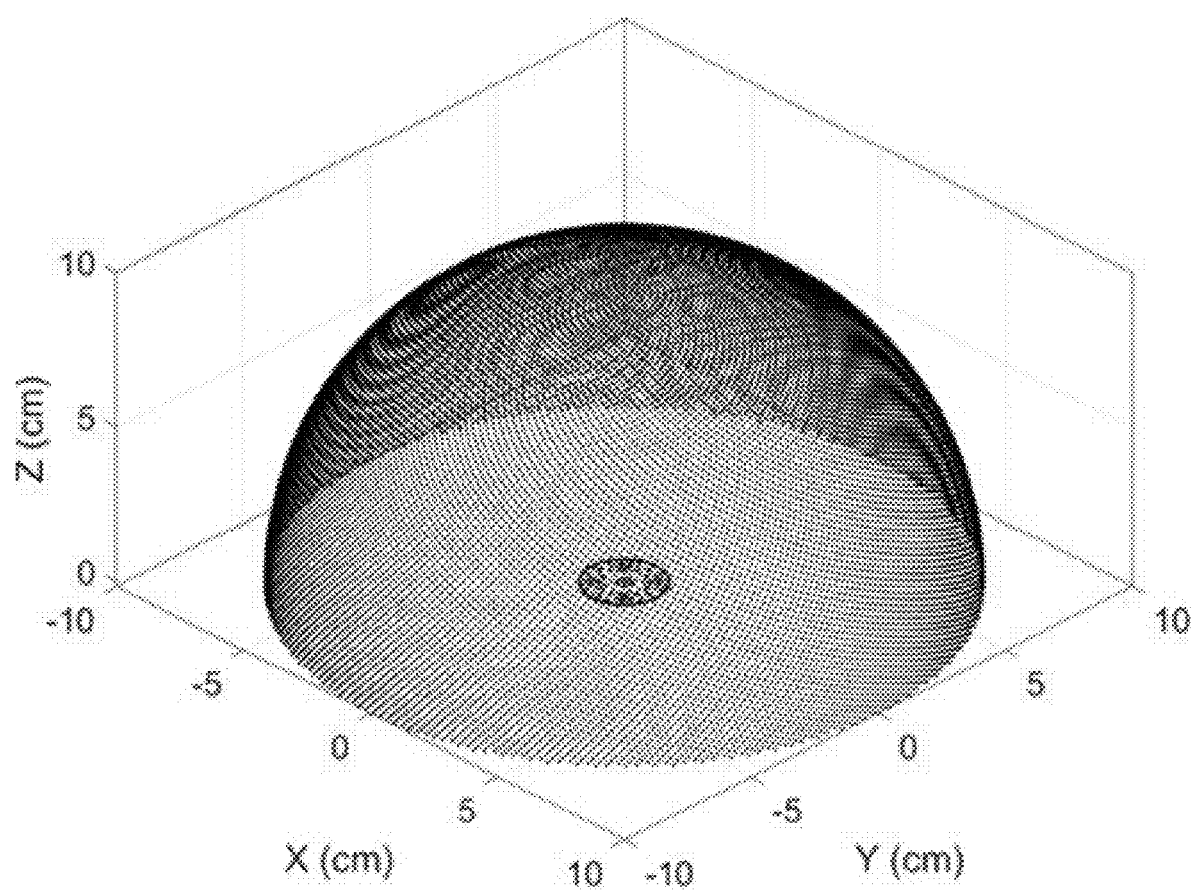
FIG. 14 illustrates an example hemispherical grid of field point samples for grating lobe analysis in the linear acoustic field simulations.

FIG. 14 shows a diagram of an example hemispherical grid of field point samples for grating lobe analysis in the linear acoustic field simulations. The sampling resolution of the grid is reduced to aid display. The canonical sparse aperture shown is located in the XY plane and centered at the origin.

To simplify visualization, the hemispherical samples are projected onto a regularly sampled 2D plane. First, the (x,y,z) Cartesian coordinates of each sample are converted to the (r, α, β) convention using the following set of equations:

$$r = \sqrt{x^2 + y^2 + z^2}$$

$$\alpha = \text{atan } 2(x, z),$$

$$\beta = \text{atan } 2(y, z)$$

where atan 2( ) is the 4-quadrant arctangent function. The resulting set of coordinates are then used to form an interpolation function using the scatteredInterpolant( ) function in MATLAB, which is evaluated to a 2D regular grid over α and β spanning ±90 degrees in each dimension.

The grating lobe performance for each optimized pair was investigated for transmit and receive steering angles up to ±45 degrees in both azimuth and elevation. Specifically, fields were generated over a hemispherical geometry as shown in FIG. 14 for (azimuth/elevation) steering angles of (0,0) degrees, (0,45) degrees, and (45,45) degrees to focal ranges of 25 mm, 50 mm, and 100 mm for the near-range, mid-range, and far-range apertures. Sidelobes and grating lobes were characterized by finding the maximum field amplitude outside of the main lobe. For steering at (0,0), the maximum field was found outside of an azimuth/elevation "radius" of 45 degrees. Similarly, for steering at (0,45), the maximum field in the opposite 2 quadrants was found. Due to symmetry, the grating lobe levels for (0,45) are the same as those for (0,±45) and (±45,0). Lastly, for steering at (45,45), the maximum field in the remaining 3 quadrants was found. Likewise, the grating lobe levels for (45,45) are the same as those for (±45,±45), (∓45,±45), and (±45,∓45). Steering in between the 45 degree range was not explored because the lobes will always be less than the values at 45 degrees.

Figure 15:
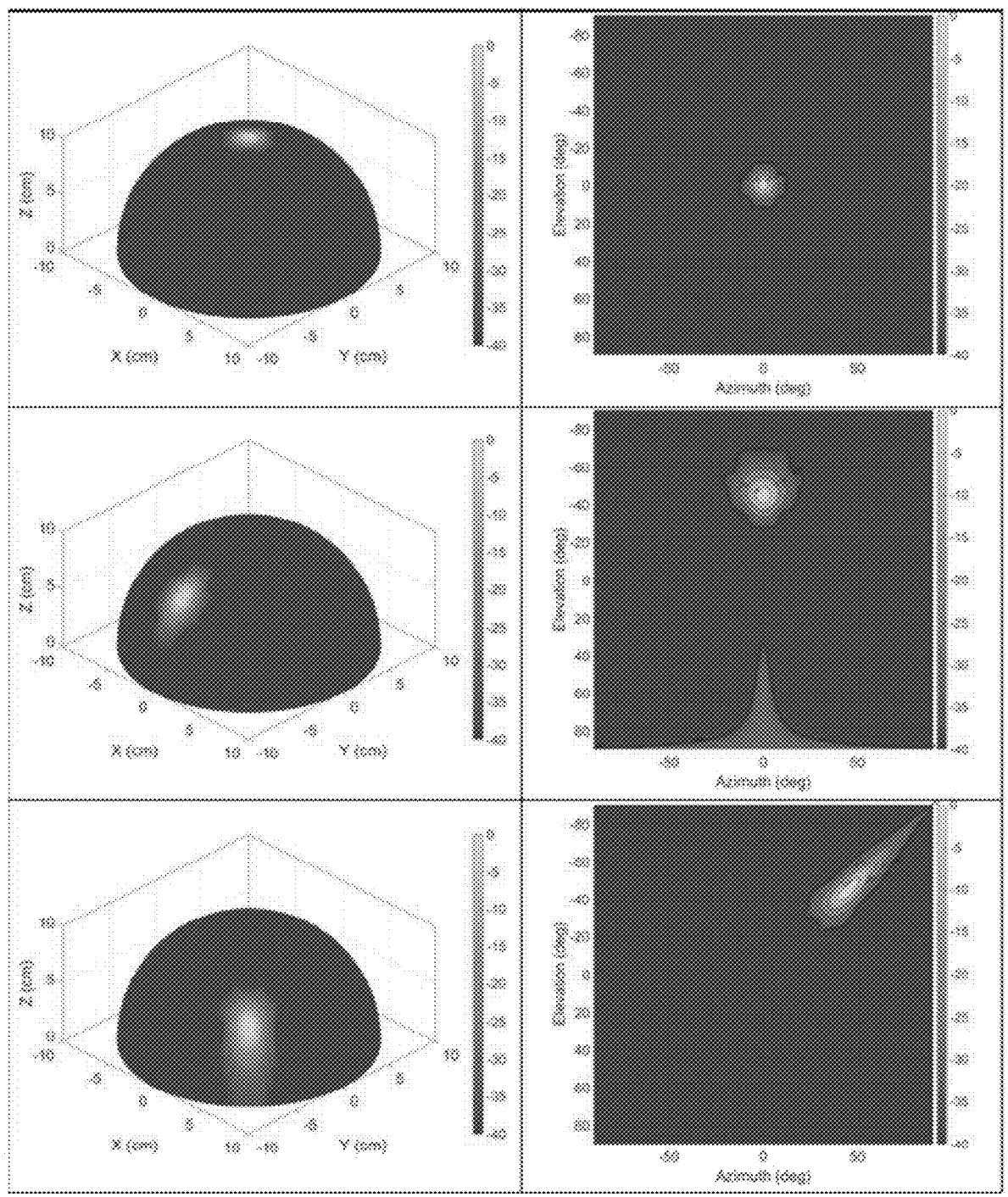
FIG. 15 illustrates example field plots for grating lobe analysis.

A set of field plots sampled on the hemispherical grid for sparse aperture set 1 focused at 100 mm and steered to (azimuth, elevation) of (0,0), (0,−45), and (45,−45) degrees is shown in FIG. 15 (left). A black dot is plotted at the requested focal point. The corresponding 2D projections of each hemispherical field onto the azimuth-elevation plane is also shown in FIG. 9 (right).

FIG. 15 shows diagrams showing example field plots for grating lobe analysis performed for sparse aperture 1 at 100 cm focusing on hemispherical grid (left) and corresponding 2D projections onto the azimuth-elevation plane (right). From top to bottom, steering is (0,0), (0,−45), and (45,−45) degrees. The grating lobe above the −40 dB level is clearly visible in the (0,−45) case. The small black dot on the hemispherical field plots is at the location of the electronic focus.

The grating lobes for all 6 apertures are tabulated in Table 2. As in the SLL optimization, sparse aperture sets 6, 11, and 12 perform the best and set 5 is only slightly behind. Sparse aperture sets 3 and 9 are an excellent choice as well given the nominal 64 RX channels. Clearly, steering towards (0,±45) and (±45,0) degrees presents the most challenge in terms of grating lobes at all depths; however, lobes in at these steep angles will almost certainly be reflected away from the aperture as discussed earlier.

Table 2 shows example grating lobe levels simulated in linear acoustic field simulations for the 6 optimized sparse apertures shown in Table 1 and FIG. 10. The best values are bolded for each array size N.

TABLE 2

| | | Maximum grating lobe levels in dB focal distance | | | | | | | | |
|---|---|---|---|---|---|---|---|---|---|---|
| | | 25 mm | | | 50 mm | | | 100 mm | | |
| azimuth/elevation | | 0/0 | 0/45 | 45/45 | 0/0 | 0/45 | 45/45 | 0/0 | 0/45 | 45/45 |
| Sparse aperture # (N) | 1 (32) | −42.91 | −30.11 | −38.99 | −47.06 | −31.34 | −40.61 | −47.13 | −31.14 | −40.80 |
| | 2 (32) | −42.34 | −28.11 | −35.52 | −48.15 | −32.52 | −41.01 | −47.40 | −32.59 | −39.63 |
| | 3 (32) | −41.06 | −28.59 | −35.20 | −43.85 | −29.93 | −37.11 | −48.75 | −31.92 | −41.78 |
| | 4 (32) | −45.99 | −29.31 | −38.34 | −47.23 | −33.30 | −42.88 | −52.08 | −34.19 | −46.02 |
| | 5 (32) | −43.20 | −29.88 | −38.38 | −49.48 | −31.77 | −44.60 | −52.80 | −34.51 | −45.71 |
| | 6 (32) | −46.12 | −29.02 | −39.44 | −52.28 | −32.94 | −45.60 | −53.92 | −35.49 | −48.15 |
| | 7 (33) | −39.17 | −31.00 | −35.91 | −45.51 | −34.10 | −39.22 | −44.30 | −33.83 | −38.15 |
| | 8 (33) | −43.73 | −29.91 | −37.91 | −49.91 | −34.27 | −42.78 | −52.39 | −34.18 | −44.24 |
| | 9 (33) | −43.64 | −30.92 | −38.68 | −47.87 | −33.27 | −40.24 | −47.84 | −35.21 | −41.14 |
| | 10 (33) | −41.89 | −30.91 | −35.00 | −48.26 | −34.10 | −41.66 | −50.03 | −35.21 | −41.02 |
| | 11 (33) | −44.76 | −31.18 | −39.51 | −49.30 | −33.26 | −43.67 | −53.28 | −36.26 | −47.67 |
| | 12 (33) | −42.19 | −31.12 | −37.48 | −49.13 | −34.39 | −45.42 | −50.39 | −36.50 | −45.76 |

In summary of the example implementations of the example CMUT-employed acoustic imaging system and methods, the CMUT enables a larger aperture (25 mm) than the example PZT aperture (10 mm) at a fraction of the cost. For example, in example implementations of imaging a body part having bone, what is gained is much better focusing, steering, and thus discrimination of normal bone reflections from extraneous scattering. Based on the example results, the imaging resolution can be improved, e.g., allowing for more accurate interpretation of the imaged volume of interest (VOI), by approximately a factor proportional to the −6 dB beamwidth at the bone. As the 11×11 example array is virtually unfocused beyond its 1.46 cm Fresnel distance, the improvement in the ability to isolate bone normals will be greatly improved with a Fresnel distance of up to 10 cm.

The challenge of a limited TX and RX channel count for such a large aperture is countered using sparse apertures for TX and RX. Optimized sparse apertures can perform nearly as well as their fully-sampled equivalents, with many fewer active elements. As the primary challenge with sparse apertures is the introduction of grating lobes, great care was taken to study grating lobes at the extrema of operation (e.g., 45 degrees steering in azimuth and/or elevation). Moreover, for some example embodiments, disclosed is a unique design where the TX and RX sparse apertures are both mutually exclusive and perform with multiple aperture openings for near-, mid-, and far-range operation. For these embodiments, for example, this functionality can accommodate many clinical situations encountered with just a single device. Integration of TX circuitry within the ASIC behind the CMUT can allow for inexpensive high channel counts (e.g., ≥256). Here, it is shown that low channel count RX can be traded for high channel count TX, e.g. 512 TX/64 RX vs. 256 TX/128 RX, which reduces cost of the receiver-side electronics by at least a factor of 2.

The example implementations and results of the example systems and methods for producing sparse apertures described herein are not exhaustive, and other sparse apertures can be produced in accordance with the present technology. Optimization of sparse apertures is complicated by exclusivity, which often times results in optimizing a suboptimal TX and/or RX aperture as they are coupled together. Many hundreds of candidates have been generated, and based on their statistics, the examples that have been found and described herein are very good. The side lobe and grating lobe performance of the sparse aperture designs presented is impressive considering all that is being asked of one small array: steering to 45 degrees in both azimuth and elevation, focusing from 2-10 cm with reasonable f/numbers, mutually exclusive TX and RX, and non-apodized TX.

In some example embodiments, the system and methods are configured to produce a CMUT aperture with nominally 512 TX elements and 64 RX elements with either 32×32 or 33×33 array size. An initial analysis of sizes >33×33 has also been performed, but has been omitted from this report due to time constraints and lack of remarkable information. There are no significant size-dependent impacts on SLLs or GLLs between 32×32 or 33×33 apertures as both are within λ/2 pitch.

Figure 16:
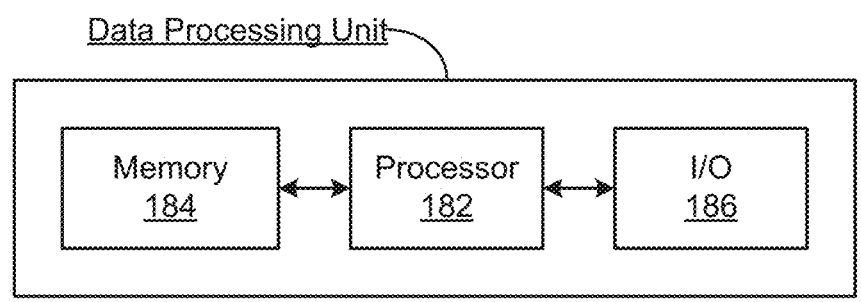
FIG. 16 shows a block diagram of an example data processing device operable to implement SSAU imaging.

FIG. 16 shows a block diagram of an example data processing device.

In some embodiments, the data processing device can be resident on one or more computers (e.g., desktop computer, laptop computer, a network of computer devices in data communication with each other via the Internet (e.g., in the 'cloud'), or other computing device including, but not limited to, a smartphone, tablet, or wearable computing/communications device).

The data processing device can include a programmable processing unit and storage device that may include, but is not limited to, the following components, e.g., one or more processors, serial processors, parallel processors, math co-processors, general purpose graphical processing units (GPUs), FPGAs, ASICSs, DSPs, nonvolatile memory, RAM, digital buffers, storage devices, hard drives, USB, FireWire, Ethernet, PCI, IEEE 1394 Serial, Wi-Fi, Fiber Channel, fiber optics, a wireless bus, a serial bus, external display adaptor, external display driver, a parallel bus, communications components, and power supply electronics. In some embodiments, for example, the data processing device may also include a display device, e.g., such as a monitor, speaker, or other device to produce a combination of visual, audio or haptic output. For example, in some embodiments, the display device may be incorporated together with the data processing device when the data processing device is resident on a computer, e.g., such as in a single unit or separately through cabling to an external display.

As shown in the example of FIG. 16, the data processing device include a processor 182 to process data and a memory 184 in communication with the processor 182 to store data. For example, the processor 182 can include a central processing unit (CPU) or a microcontroller unit (MCU). For example, the memory 184 can include processor-executable code, which when executed by the processor 182, configures the data processing device to perform various operations, such as receiving information, commands, and/or data, processing information and data, and transmitting or providing information/data to another entity (e.g., external device). To support various functions of the data processing device, the memory 184 can store other information and data, such as instructions, software, values, images, and other data processed or referenced by the processor 182. Various types of Random Access Memory (RAM) devices, Read Only Memory (ROM) devices, Flash Memory devices, and other suitable storage media can be used to implement storage functions of the memory 184. The memory 184 can store data and information of the data processing device and other units of a device in communication with the data processing device. For example, the memory 184 can store device unit parameters, and hardware constraints, as well as software parameters and programs for operation on such a device in communication with the data processing device. In this example, the data processing device includes an I/O unit 186 that can allow communicative connectability of the data processing device to other units of other device(s). For example, I/O unit 186 can provide the data processing device to be in communications with other devices or systems, e.g., using various types of wired or wireless interfaces compatible with typical data communication standards, for example, including, but not limited to, Universal Serial Bus (USB), IEEE 1394 (FireWire), Bluetooth, IEEE 802.111, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE/5G cellular communication methods, and parallel interfaces. The I/O unit 186 can also provide communicative connectability of the data processing device to an external interface (e.g., of an external device), source of data storage, or display device. The I/O unit 182 of the data processing device can also interface with other external interfaces, sources of data storage, and/or visual or audio display devices, etc., to retrieve and transfer data and information that can be processed by the processor 182, stored in the memory 184, or exhibited on an output unit of a device in communication with the data processing device.

Figure 17:
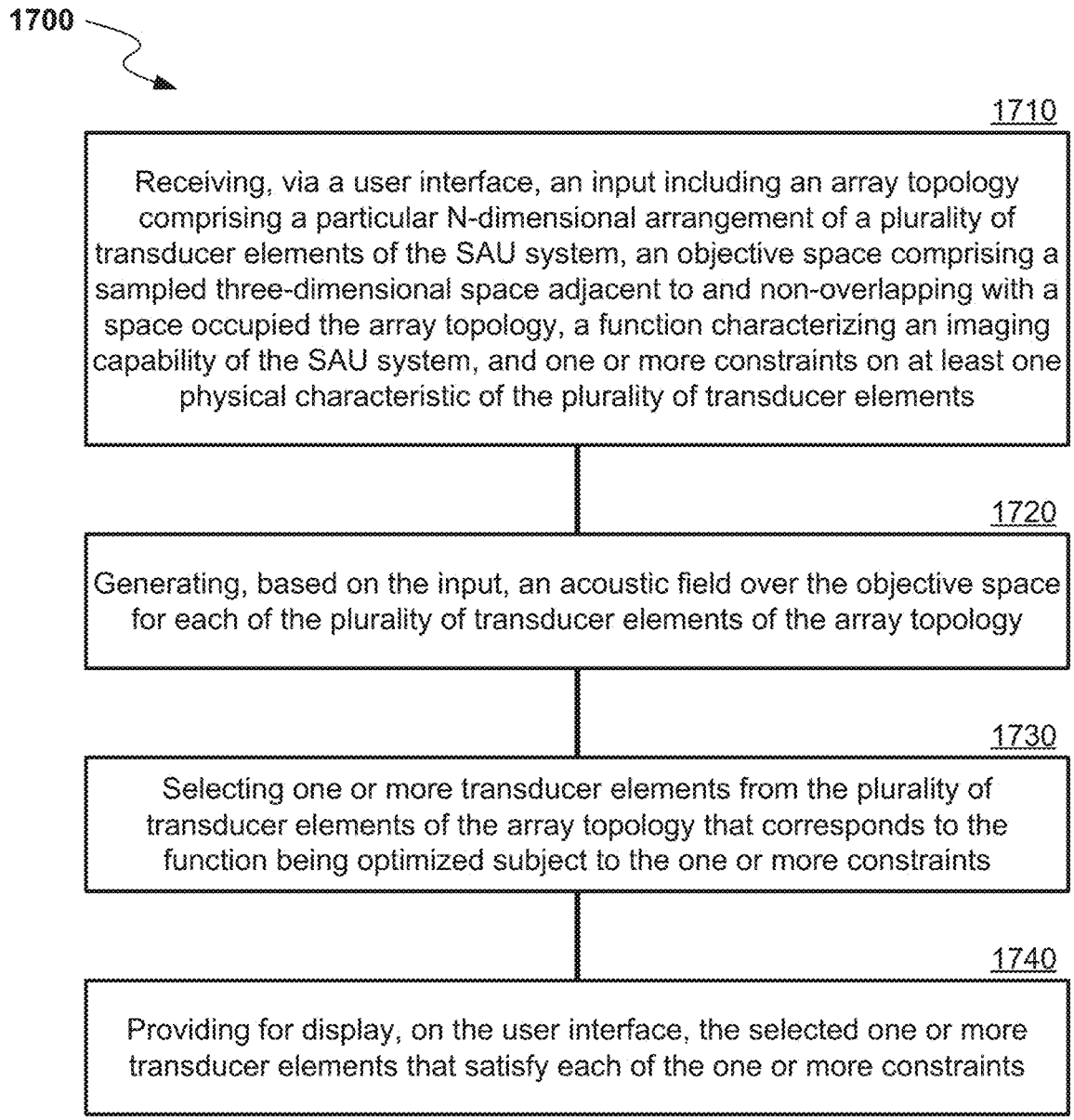
FIG. 17 is a flowchart of an example method for SSAU imaging in accordance with the present technology.

FIG. 17 is a flowchart of an example method for SSAU imaging. The method 1700 includes, at operation 1710, receiving, via a user interface, an input including an array topology comprising a particular N-dimensional arrangement of a plurality of transducer elements of the SAU system, an objective space comprising a sampled three-dimensional space adjacent to and non-overlapping with a space occupied the array topology, a function characterizing an imaging capability of the SAU system, and one or more constraints on at least one physical characteristic of the plurality of transducer elements, wherein N is a positive integer.

The method 1700 includes, at operation 1720, generating, based on the input, an acoustic field over the objective space for each of the plurality of transducer elements of the array topology. In some embodiments, the acoustic field may be pre-computed.

The method 1700 includes, at operation 1730, selecting one or more transducer elements from the plurality of transducer elements of the array topology that corresponds to the function being optimized subject to the one or more constraints, the one or more transducer elements corresponding to a plurality of transmit apertures and a plurality of receive apertures.

In some embodiments, the function that characterizes the imaging capability of the SAU system may be an objective function, a loss function or cost function (with the optimization being a minimization), a utility function or fitness function (with the optimization being a maximization). In an example, the optimization of the function corresponds to the selection of the best available transmit and receive apertures (with regard to some criterion, e.g., the imaging capability of the SAU system) from some set of available alternatives (e.g., the plurality of transducer elements of the array topology). In another example, the "best available" solution may be a function of one or more system parameters, e.g., the resolution, tolerance, or requirements of the SAU imaging system. In yet another example, the "best available" solution may not coincide with an optimal solution, e.g., the optimal solution may require a resolution that is not available in the current system, and thus a sub-optimal solution is the best available solution that is generated by performing the optimizing recited in operation 1730.

The method 1700 includes, at operation 1740, providing for display, on the user interface, the selected one or more transducer elements that satisfy each of the one or more constraints.

In some embodiments, the input further includes a target region within the objective space, and wherein each of the plurality of transmit apertures and each of the plurality of receive apertures comprises a main lobe and one or more sidelobes.

In some embodiments, the one or more transducer elements are selected such that the main lobe of each transducer element of the one or more transducer elements is directed at the target region, and the one or more sidelobes of the each transducer element are substantially suppressed at a far-field transition of the array topology when each of the plurality of transducer elements is populated.

In some embodiments, the objective space comprises a hemispherical volume, the array topology is centered a base of the hemispherical volume, and a radius of the hemispherical volume is based on the far-field transition of the array topology when each of the plurality of transducer elements is populated.

In some embodiments, each of the plurality of transmit apertures overlaps with a corresponding each of the plurality of receive apertures. In other embodiments, at least one of the plurality of transmit apertures overlaps with at least one of the plurality of receive apertures. In yet other embodiments, the plurality of transmit apertures and the plurality of receive apertures are non-overlapping.

In some embodiments, the function being optimized is based on an optimization algorithm that comprises at least one of a simulated annealing algorithm, a gradient descent algorithm, a genetic algorithm, or a fractal-based optimization technique.

In some embodiments, the method 1700 further comprises the operation of selecting, prior to selecting the one or more transducer elements, an initial set of transducer elements from the plurality of transducer elements in a random manner and subject to the one or more constraints, wherein the optimization algorithm uses the initial set of transducer elements as a seed value to begin optimizing the function.

In some embodiments, the one or more constraints comprises a limit on a number of the plurality of transmit apertures that are adjacent to each other.

In some embodiments, a number of the plurality of transmit apertures and the plurality of receive apertures is ≤50% than a number of the plurality of transducer elements.

In some embodiments, a number of the plurality of transmit apertures is greater than or equal to two times a number of the plurality of receive apertures.

In some embodiments, N=3.

In some embodiments, the at least one physical characteristic comprises each of the plurality of transducer elements being configured to operate only as a transmitter, only as a receiver, or both as a transmitter and a receiver.

According to some embodiments of the disclosed technology, a sparse array is usable for both transmission and reception such that undesirable coherent lobe energy outside of the main lobe is suppressed for a plurality of points in space by optimizing locations of transmit elements and receive elements.

In some embodiments, the array is operable as a synthetic transmit aperture.

In some embodiments, the array is operable as a non-synthetic transmit aperture.

In some embodiments, the main lobe is focused on a plurality of points in space.

In some embodiments, the optimized transmit and receive apertures are fully-overlapping, partially-overlapping, or non-overlapping.

In some embodiments, the optimized number of transmit elements is twice or greater than the number of receive elements.

In some embodiments, the area of active array elements is 50% or less than the area of a fully-sampled array.

In some embodiments, the apodization on both transmission and reception is unity.

In some embodiments, the undesirable coherent lobe energy is suppressed for points in space lying on a hemispherical surface, wherein the sparse array is centered at the base of the hemisphere, and radius of the hemisphere is placed at the location of the far-field transition (Fresnel distance) of the fully-sampled transmit-receive aperture.

In some embodiments, the undesirable coherent lobe energy is suppressed for points in space lying within a hemispherical volume, wherein the sparse array is centered at the base of the hemispherical volume, wherein the radius is determined by the far-field transition (Fresnel distance) of the fully-sampled transmit-receive array.

In some embodiments, one or more sparse sub-arrays within the sparse array are optimized over hemispherical surfaces with radii determined by the respective far-field transitions of the respective fully-sampled transmit-receive arrays.

In some embodiments, one or more sparse sub-arrays within the sparse array are optimized over hemispherical volumes with radii determined by the respective far-field transitions of the respective fully-sampled transmit-receive arrays.

According to some embodiments of the disclosed technology, a method for optimizing a sparse array for ultrasound imaging comprises a set of elements placed within an arbitrary array topology, wherein the element placement is subject to constraints, an objective space, an objective function, and an optimizer that evaluates the objection function in the objective space to optimize the element placement.

In some embodiments, the objective function is consists of a field simulator.

In some embodiments, the simulated fields are precomputed.

In some embodiments, the element locations within the sparse aperture are randomly seeded subject to constraints.

In some embodiments, the objected function is minimized using an optimizer such that undesirable lobe energy is suppressed over the objective space, subject to constraints.

In some embodiments, the constraints limit the number of adjacent elements.

In some embodiments, the constraints enforce empty space between elements.

Figure 18:
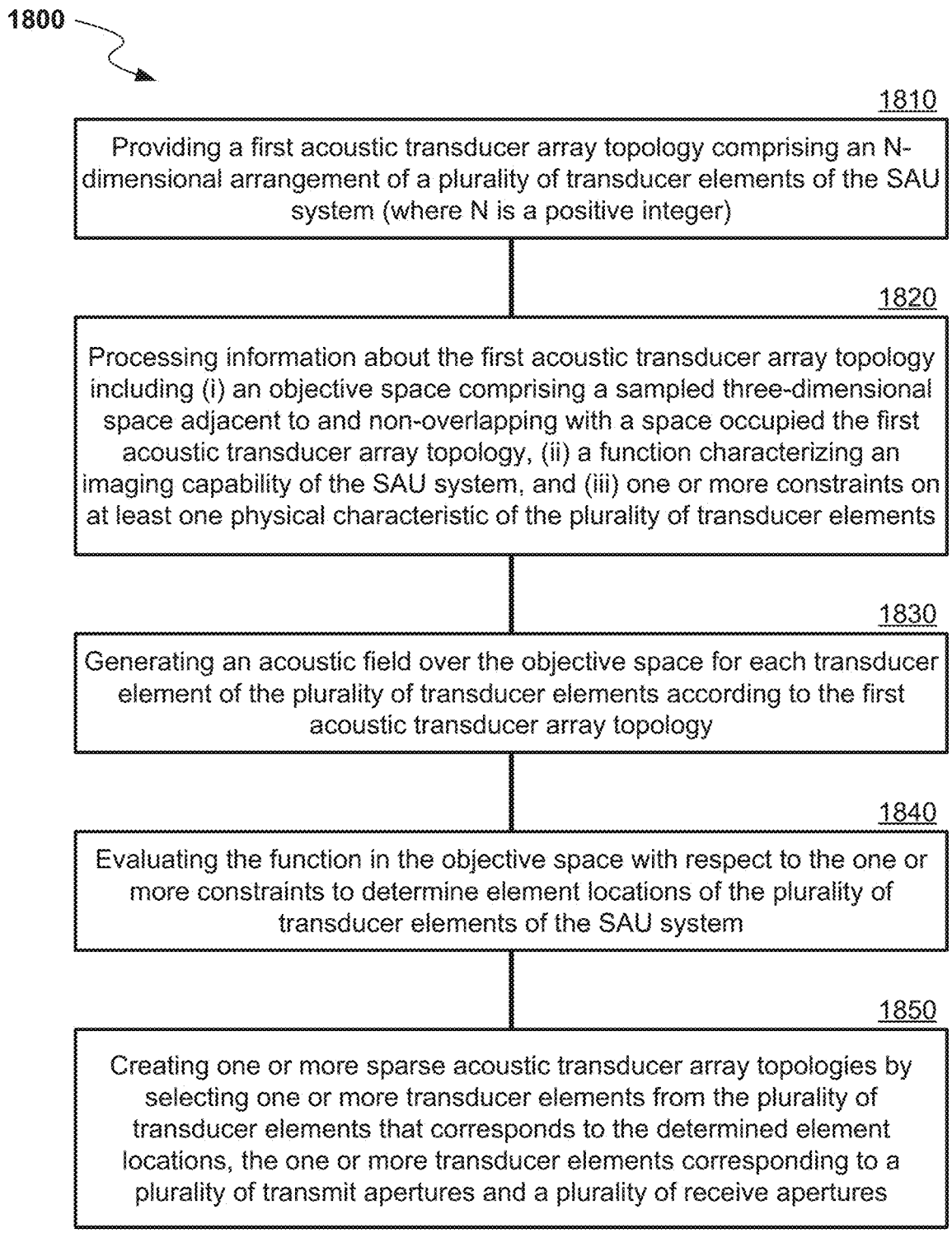
FIG. 18 shows a diagram illustrating an example embodiment of a method for producing a synthetic aperture ultrasound system, in accordance with the disclosed technology.

FIG. 18 shows a diagram illustrating an example embodiment of a method for producing a synthetic aperture ultrasound system, labeled 1800, in accordance with the disclosed technology. The method 1800 includes, at operation 1810, providing a first acoustic transducer array topology comprising an N-dimensional arrangement of a plurality of transducer elements of the SAU system (where N is a positive integer). The method 1800 includes, at operation 1820, processing information about the first acoustic transducer array topology including (i) an objective space comprising a sampled three-dimensional space adjacent to and non-overlapping with a space occupied the first acoustic transducer array topology, (ii) a function characterizing an imaging capability of the SAU system, and (iii) one or more constraints on at least one physical characteristic of the plurality of transducer elements. The method 1800 includes, at operation 1830, generating an acoustic field over the objective space for each transducer element of the plurality of transducer elements according to the first acoustic transducer array topology. The method 1800 includes, at operation 1840, evaluating the function in the objective space with respect to the one or more constraints to optimize element locations of plurality of transducer elements of the SAU system. The method 1800 includes, at operation 1850, creating one or more sparse acoustic transducer array topologies by selecting one or more transducer elements from the plurality of transducer elements that corresponds to the determined element locations, the one or more transducer elements corresponding to a plurality of transmit apertures and a plurality of receive apertures.

In some embodiments of the method 1800, for example, the method 1800 includes one or more of the following features. For example, in some embodiments of the method 1800, the information about the first acoustic transducer array topology further includes a target region within the objective space, wherein each of the plurality of transmit apertures and each of the plurality of receive apertures comprises a main lobe and one or more sidelobes. For example, in some embodiments of the method 1800, for the one or more sparse acoustic transducer array topologies, the one or more transducer elements are selected such that the main lobe of each transducer element of the one or more transducer elements is directed at the target region, and wherein the one or more sidelobes of the each transducer element are substantially suppressed at a far-field transition of the array topology when each of the plurality of transducer elements is populated. For example, in some embodiments of the method 1800, the objective space comprises a hemispherical volume, wherein the first acoustic transducer array topology is centered a base of the hemispherical volume, and wherein a radius of the hemispherical volume is based on the far-field transition of the first acoustic transducer array topology when each of the plurality of transducer elements is populated. For example, in some embodiments of the method 1800, each of the plurality of transmit apertures overlaps with a corresponding each of the plurality of receive apertures. For example, in some embodiments of the method 1800, at least one of the plurality of transmit apertures overlaps with at least one of the plurality of receive apertures. For example, in some embodiments of the method 1800, the plurality of transmit apertures and the plurality of receive apertures are non-overlapping. For example, in some embodiments of the method 1800, the evaluating the function includes optimizing an objective function based on an optimization algorithm that comprises at least one of a simulated annealing algorithm, a gradient descent algorithm, a genetic algorithm, or a fractal-based optimization technique. For example, in some embodiments of the method 1800, the method 1800 further comprises: prior to selecting the one or more transducer elements, selecting an initial set of transducer elements from the plurality of transducer elements in a random manner and subject to the one or more constraints, wherein the optimization algorithm uses the initial set of transducer elements as a seed value to begin optimizing the function. For example, in some embodiments of the method 1800, the one or more constraints comprises a limit on a number of the plurality of transmit apertures that are adjacent to each other. For example, in some embodiments of the method 1800, a number of the plurality of transmit apertures and the plurality of receive apertures is 50% or less than a number of the plurality of transducer elements. For example, in some embodiments of the method 1800, a number of the plurality of transmit apertures and the plurality of receive apertures is 15% or less than a number of the plurality of transducer elements. For example, in some embodiments of the method 1800, a number of the plurality of transmit apertures is greater than or equal to two times a number of the plurality of receive apertures. For example, in some embodiments of the method 1800, the N-dimensional arrangement of the plurality of transducer elements of the SAU system includes a one-dimensional arrangement, a two-dimensional arrangement, or a three-dimensional arrangement. For example, in some embodiments of the method 1800, the at least one physical characteristic comprises each of the plurality of transducer elements being configured to operate only as a transmitter, only as a receiver, or both as a transmitter and a receiver. For example, in some embodiments of the method 1800, the function characterizing the imaging capability includes information on at least one of an objective function, a loss function or cost function where evaluating the function in the objective space corresponds to a minimization, or a utility function or fitness function where evaluating the function in the objective space corresponds to a maximization. For example, in some embodiments of the method 1800, the imaging capability of the SAU system includes one or more of desired point spread function parameters, desired side-lobe levels, desired grating lobe levels, or desired fraction of power transmitted in main lobe. For example, in some embodiments of the method 1800, the method 1800 further comprises: providing for display, on a user interface, the selected one or more transducer elements that satisfy each of the one or more constraints.

Examples

In some embodiments in accordance with the present technology (example A1), a method for producing a synthetic aperture ultrasound (SAU) system for ultrasound imaging includes providing a first acoustic transducer array topology comprising an N-dimensional arrangement of a plurality of transducer elements of the SAU system, wherein N is a positive integer; processing information about the first acoustic transducer array topology including (i) an objective space comprising a sampled three-dimensional space adjacent to and non-overlapping with a space occupied the first acoustic transducer array topology, (ii) a function characterizing an imaging capability of the SAU system, and (iii) one or more constraints on at least one physical characteristic of the plurality of transducer elements; generating an acoustic field over the objective space for each transducer element of the plurality of transducer elements according to the first acoustic transducer array topology; evaluating the function in the objective space with respect to the one or more constraints to determine element locations of the plurality of transducer elements of the SAU system; and creating one or more sparse acoustic transducer array topologies by selecting one or more transducer elements from the plurality of transducer elements that corresponds to the determined element locations, the one or more transducer elements corresponding to a plurality of transmit apertures and a plurality of receive apertures.

Example A2 includes the method of any of examples A1-A18, wherein the information about the first acoustic transducer array topology further includes a target region within the objective space, wherein each of the plurality of transmit apertures and each of the plurality of receive apertures comprises a main lobe and one or more sidelobes.

Example A3 includes the method of example A2 or any of examples A1-A18, wherein, for the one or more sparse acoustic transducer array topologies, the one or more transducer elements are selected such that the main lobe of each transducer element of the one or more transducer elements is directed at the target region, and wherein the one or more sidelobes of the each transducer element are substantially suppressed at a far-field transition of the array topology when each of the plurality of transducer elements is populated.

Example A4 includes the method of example A3 or any of examples A1-A18, wherein the objective space comprises a hemispherical volume, wherein the first acoustic transducer array topology is centered a base of the hemispherical volume, and wherein a radius of the hemispherical volume is based on the far-field transition of the first acoustic transducer array topology when each of the plurality of transducer elements is populated.

Example A5 includes the method of any of examples A1-A18, wherein each of the plurality of transmit apertures overlaps with a corresponding each of the plurality of receive apertures.

Example A6 includes the method of any of examples A1-A18, wherein at least one of the plurality of transmit apertures overlaps with at least one of the plurality of receive apertures.

Example A7 includes the method of any of examples A1-A18, wherein the plurality of transmit apertures and the plurality of receive apertures are non-overlapping.

Example A8 includes the method of any of examples A1-A18, wherein the evaluating the function includes optimizing an objective function based on an optimization algorithm that comprises at least one of a simulated annealing algorithm, a gradient descent algorithm, a genetic algorithm, or a fractal-based optimization technique.

Example A9 includes the method of example A8 or any of examples A1-A18, wherein the method further comprises: prior to selecting the one or more transducer elements, selecting an initial set of transducer elements from the plurality of transducer elements in a random manner and subject to the one or more constraints, wherein the optimization algorithm uses the initial set of transducer elements as a seed value to begin optimizing the function.

Example A10 includes the method of any of examples A1-A18, wherein the one or more constraints comprises a limit on a number of the plurality of transmit apertures that are adjacent to each other.

Example A11 includes the method of any of examples A1-A18, wherein a number of the plurality of transmit apertures and the plurality of receive apertures is 50% or less than a number of the plurality of transducer elements.

Example A12 includes the method of any of examples A1-A18, wherein a number of the plurality of transmit apertures and the plurality of receive apertures is 15% or less than a number of the plurality of transducer elements.

Example A13 includes the method of any of examples A1-A18, wherein a number of the plurality of transmit apertures is greater than or equal to two times a number of the plurality of receive apertures.

Example A14 includes the method of any of examples A1-A18, wherein the N-dimensional arrangement of the plurality of transducer elements of the SAU system includes a one-dimensional arrangement, a two-dimensional arrangement, or a three-dimensional arrangement.

Example A15 includes the method of any of examples A1-A18, wherein the at least one physical characteristic comprises each of the plurality of transducer elements being configured to operate only as a transmitter, only as a receiver, or both as a transmitter and a receiver.

Example A16 includes the method of any of examples A1-A18, wherein the function characterizing the imaging capability includes information on at least one of an objective function, a loss function or cost function where evaluating the function in the objective space corresponds to a minimization, or a utility function or fitness function where evaluating the function in the objective space corresponds to a maximization.

Example A17 includes the method of any of examples A1-A18, wherein the imaging capability of the SAU system includes one or more of desired point spread function parameters, desired side-lobe levels, desired grating lobe levels, or desired fraction of power transmitted in main lobe.

Example A18 includes the method of any of examples A1-A18, wherein the method further comprises: providing for display, on a user interface, the selected one or more transducer elements that satisfy each of the one or more constraints.

In some embodiments in accordance with the present technology (example A19), a device for determining synthetic aperture ultrasound (SAU) transducer topology includes a data processing system comprising one or more processors, and one or more storage devices comprising processor-executable instructions that, responsive to execution by the one or more processors, cause the system to perform operations for determining a synthetic aperture ultrasound transducer system for sparse SAU ultrasound imaging, where the operations comprise: receiving data associated with a first acoustic transducer array topology comprising an N-dimensional arrangement of the plurality of transducer elements of the SAU system, wherein N is a positive integer; processing the data including information about the first acoustic transducer array topology that includes (i) an objective space comprising a sampled three-dimensional space adjacent to and non-overlapping with a space occupied the first acoustic transducer array topology, (ii) a function characterizing an imaging capability of the SAU system, and (iii) one or more constraints on at least one physical characteristic of the plurality of transducer elements; generating an acoustic field over the objective space for each transducer element of the plurality of transducer elements according to the first acoustic transducer array topology; evaluating the function in the objective space with respect to the one or more constraints to determine element locations of the plurality of transducer elements of the SAU system; and creating one or more sparse acoustic transducer array topologies by selecting one or more transducer elements from the plurality of transducer elements that corresponds to the determined element locations, the one or more transducer elements corresponding to a plurality of transmit apertures and a plurality of receive apertures.

In some embodiments in accordance with the present technology (example A20), a synthetic aperture ultrasound (SAU) imaging system includes a plurality of acoustic transducer elements configured to transmit acoustic signals as transmit apertures, receive acoustic signals as receive apertures, or transmit and receive acoustic signals; wherein: the plurality of acoustic transducer elements form a sparse acoustic transducer array topology generated by determining locations of the acoustic transducer elements in accordance with one or more constraints on at least one physical characteristic of the plurality of transducer elements. Each of the plurality of transmit apertures overlaps with a corresponding each of the plurality of receive apertures; or at least one of the plurality of transmit apertures overlaps with at least one of the plurality of receive apertures; or the plurality of transmit apertures and the plurality of receive apertures are non-overlapping.

Example A21 includes the SAU imaging system of example A20, wherein the locations of the acoustic transducer elements are determined by: processing information about a first acoustic transducer array topology including (i) an objective space comprising a sampled three-dimensional space adjacent to and non-overlapping with a space occupied the first acoustic transducer array topology, (ii) a function characterizing an imaging capability of the SAU imaging system, and (iii) the one or more constraints on the at least one physical characteristic of the plurality of transducer elements; generating an acoustic field over the objective space for each transducer element of the plurality of transducer elements according to the first acoustic transducer array topology; and evaluating the function in the objective space with respect to the one or more constraints to create the sparse acoustic transducer array topology by selecting one or more transducer elements from the plurality of transducer elements that corresponds to the determined element locations.

Example A22 includes the SAU imaging system of any of examples A20-A21, wherein a number of the plurality of transmit apertures and the plurality of receive apertures is one of: (a) 15% or less than a number of the plurality of transducer elements, or (b) 50% or less than a number of the plurality of transducer elements.

In some embodiments in accordance with the present technology (example A23), a non-transitory computer readable medium having executable computer code stored thereon, the executable computer code comprising instructions for optimizing a synthetic aperture ultrasound (SAU) system for ultrasound imaging, which are configured to cause a processor to perform operations, which includes providing a first acoustic transducer array topology comprising an N-dimensional arrangement of a plurality of transducer elements of the SAU system, wherein N is a positive integer; processing information about the first acoustic transducer array topology including (i) an objective space comprising a sampled three-dimensional space adjacent to and non-overlapping with a space occupied the first acoustic transducer array topology, (ii) a function characterizing an imaging capability of the SAU system, and (iii) one or more constraints on at least one physical characteristic of the plurality of transducer elements; generating an acoustic field over the objective space for each transducer element of the plurality of transducer elements according to the first acoustic transducer array topology; evaluating the function in the objective space with respect to the one or more constraints to optimize element locations of plurality of transducer elements of the SAU system; and creating an optimized acoustic transducer array topology by selecting one or more transducer elements from the plurality of transducer elements that corresponds to the optimized element locations, the one or more transducer elements corresponding to a plurality of transmit apertures and a plurality of receive apertures.

Example A24 includes the SAU system of example A23, wherein the non-transitory computer readable medium, including the instructions for optimizing the SAU system for ultrasound imaging, includes one or more features of any of examples A1-A18.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method for producing a synthetic aperture ultrasound (SAU) system for ultrasound imaging, comprising:
providing a first acoustic transducer array topology comprising an N-dimensional arrangement of a plurality of transducer elements of the SAU system, wherein N is a positive integer;
processing information about the first acoustic transducer array topology including (i) an objective space comprising a sampled three-dimensional space adjacent to and non-overlapping with a space occupied the first acoustic transducer array topology, (ii) a function characterizing an imaging capability of the SAU system, and (iii) one or more constraints on at least one physical characteristic of the plurality of transducer elements;
generating an acoustic field over the objective space for each transducer element of the plurality of transducer elements according to the first acoustic transducer array topology;
evaluating the function in the objective space with respect to the one or more constraints to determine element locations of the plurality of transducer elements of the SAU system; and
creating one or more sparse acoustic transducer array topologies by selecting one or more transducer elements from the plurality of transducer elements that corresponds to the determined element locations, the one or more transducer elements corresponding to a plurality of transmit apertures and a plurality of receive apertures.

2. The method of claim 1, wherein the information about the first acoustic transducer array topology further includes a target region within the objective space, wherein each of the plurality of transmit apertures and each of the plurality of receive apertures comprises a main lobe and one or more sidelobes.

3. The method of claim 2, wherein, for the one or more sparse acoustic transducer array topologies, the one or more transducer elements are selected such that the main lobe of each transducer element of the one or more transducer elements is directed at the target region, and wherein the one or more sidelobes of each transducer element are substantially suppressed at a far-field transition of the array topology when each of the plurality of transducer elements is populated.

4. The method of claim 3, wherein the objective space comprises a hemispherical volume, wherein the first acoustic transducer array topology is centered a base of the hemispherical volume, and wherein a radius of the hemispherical volume is based on the far-field transition of the first acoustic transducer array topology when each of the plurality of transducer elements is populated.

5. The method of claim 1, wherein each of the plurality of transmit apertures overlaps with a corresponding each of the plurality of receive apertures.

6. The method of claim 1, wherein at least one of the plurality of transmit apertures overlaps with at least one of the plurality of receive apertures.

7. The method of claim 1, wherein the plurality of transmit apertures and the plurality of receive apertures are non-overlapping.

8. The method of claim 1, wherein the evaluating the function includes optimizing an objective function based on an optimization algorithm that comprises at least one of a simulated annealing algorithm, a gradient descent algorithm, a genetic algorithm, or a fractal-based optimization technique.

9. The method of claim 8, further comprising:
prior to selecting the one or more transducer elements, selecting an initial set of transducer elements from the plurality of transducer elements in a random manner and subject to the one or more constraints,
wherein the optimization algorithm uses the initial set of transducer elements as a seed value to begin optimizing the function.

10. The method of claim 1, wherein the one or more constraints comprises a limit on a number of the plurality of transmit apertures that are adjacent to each other.

11. The method of claim 1, wherein a number of the plurality of transmit apertures and the plurality of receive apertures is 50% or less than a number of the plurality of transducer elements.

12. The method of claim 1, wherein a number of the plurality of transmit apertures and the plurality of receive apertures is 15% or less than a number of the plurality of transducer elements.

13. The method of claim 1, wherein a number of the plurality of transmit apertures is greater than or equal to two times a number of the plurality of receive apertures.

14. The method of claim 1, wherein the at least one physical characteristic comprises each of the plurality of transducer elements being configured to operate only as a transmitter, only as a receiver, or both as a transmitter and a receiver.

15. The method of claim 1, wherein the function characterizing the imaging capability includes information on at least one of an objective function, a loss function or cost function where evaluating the function in the objective space corresponds to a minimization, or a utility function or fitness function where evaluating the function in the objective space corresponds to a maximization.

16. The method of claim 1, wherein the imaging capability of the SAU system includes one or more of desired point spread function parameters, desired side-lobe levels, desired grating lobe levels, or desired fraction of power transmitted in main lobe.

17. A device for determining synthetic aperture ultrasound (SAU) transducer topology comprising:
a data processing system comprising one or more processors, and one or more storage devices comprising processor-executable instructions that, responsive to execution by the one or more processors, cause the system to perform operations for determining a synthetic aperture ultrasound transducer system for sparse SAU ultrasound imaging, the operations comprising:
receiving data associated with a first acoustic transducer array topology comprising an N-dimensional arrangement of the plurality of transducer elements of the SAU system, wherein N is a positive integer;
processing the data including information about the first acoustic transducer array topology that includes (i) an objective space comprising a sampled three-dimensional space adjacent to and non-overlapping with a space occupied the first acoustic transducer array topology, (ii) a function characterizing an imaging capability of the SAU system, and (iii) one or more constraints on at least one physical characteristic of the plurality of transducer elements;

generating an acoustic field over the objective space for each transducer element of the plurality of transducer elements according to the first acoustic transducer array topology;

evaluating the function in the objective space with respect to the one or more constraints to determine element locations of plurality of transducer elements of the SAU system; and creating one or more sparse acoustic transducer array topologies by selecting one or more transducer elements from the plurality of transducer elements that corresponds to the determined element locations, the one or more transducer elements corresponding to a plurality of transmit apertures and a plurality of receive apertures.

18. A synthetic aperture ultrasound (SAU) imaging system, comprising:

a plurality of acoustic transducer elements configured to transmit acoustic signals as transmit apertures, receive acoustic signals as receive apertures, or transmit and receive acoustic signals; wherein:

the plurality of acoustic transducer elements form a sparse acoustic transducer array topology generated by determining locations of the acoustic transducer elements in accordance with one or more constraints on at least one physical characteristic of the plurality of transducer elements; and each of the plurality of transmit apertures overlaps with a corresponding each of the plurality of receive apertures; or at least one of the plurality of transmit apertures overlaps with at least one of the plurality of receive apertures; or the plurality of transmit apertures and the plurality of receive apertures are non-overlapping, wherein the locations of the acoustic transducer elements are determined by:

processing information about a first acoustic transducer array topology including (i) an objective space comprising a sampled three-dimensional space adjacent to and non-overlapping with a space occupied the first acoustic transducer array topology, (ii) a function characterizing an imaging capability of the SAU imaging system, and (iii) the one or more constraints on the at least one physical characteristic of the plurality of transducer elements;

generating an acoustic field over the objective space for each transducer element of the plurality of transducer elements according to the first acoustic transducer array topology; and evaluating the function in the objective space with respect to the one or more constraints to create the sparse acoustic transducer array topology by selecting one or more transducer elements from the plurality of transducer elements that corresponds to the determined element locations.

19. A synthetic aperture ultrasound (SAU) imaging system, comprising:

a plurality of acoustic transducer elements configured to transmit acoustic signals as transmit apertures, receive acoustic signals as receive apertures, or transmit and receive acoustic signals; wherein:

the plurality of acoustic transducer elements form a sparse acoustic transducer array topology generated by determining locations of the acoustic transducer elements in accordance with one or more constraints on at least one physical characteristic of the plurality of transducer elements; and each of the plurality of transmit apertures overlaps with a corresponding each of the plurality of receive apertures; or at least one of the plurality of transmit apertures overlaps with at least one of the plurality of receive apertures; or the plurality of transmit apertures and the plurality of receive apertures are non-overlapping, wherein a number of the plurality of transmit apertures and the plurality of receive apertures is one of: (a) 15% or less than a number of the plurality of transducer elements, or (b) 50% or less than a number of the plurality of transducer elements.

* * * * *